United States Patent [19]
Wong et al.

[11] Patent Number: 4,783,337
[45] Date of Patent: * Nov. 8, 1988

[54] OSMOTIC SYSTEM COMPRISING PLURALITY OF MEMBERS FOR DISPENSING DRUG

[75] Inventors: Patrick S.-L. Wong, Hayward; Brian L. Barclay, Sunnyvale; Joseph C. Oeters, Mountain View; Felix Theeuwes, Los Altos, all of Calif.

[73] Assignee: ALZA Corporation, Palo Alto, Calif.

[ * ] Notice: The portion of the term of this patent subsequent to Sep. 16, 2003 has been disclaimed.

[21] Appl. No.: 912,712

[22] Filed: Sep. 29, 1986

Related U.S. Application Data

[63] Continuation-in-part of Ser. No. 685,687, Dec. 24, 1984, abandoned, which is a continuation-in-part of Ser. No. 493,760, May 11, 1983, abandoned.

[51] Int. Cl.$^4$ .......................... A61K 9/22; A61M 31/00
[52] U.S. Cl. ..................................... 424/468; 424/469; 424/474; 424/486; 428/320.2; 428/913; 604/892.1
[58] Field of Search ............... 604/890, 891, 892, 893, 604/894, 895, 896; 424/468, 469, 474, 486; 428/320.2, 913

[56] References Cited

U.S. PATENT DOCUMENTS

| | | | |
|---|---|---|---|
| 4,008,719 | 2/1977 | Theeuwes et al. | 128/260 |
| 4,014,334 | 3/1977 | Theeuwes et al. | 128/260 |
| 4,063,064 | 12/1977 | Saunders et al. | 219/121 |
| 4,077,407 | 3/1978 | Theeuwes et al. | 128/260 |
| 4,093,708 | 6/1978 | Zaffaroni et al. | 424/15 |
| 4,100,098 | 4/1980 | Ayer et al. | 128/260 |
| 4,111,202 | 9/1980 | Theeuwes | 128/260 |
| 4,186,184 | 1/1980 | Zaffaroni | 424/14 |
| 4,210,139 | 7/1980 | Higuchi | 128/260 |
| 4,224,427 | 9/1980 | Mueller et al. | 526/930 |
| 4,285,987 | 8/1981 | Ayer et al. | 427/3 |
| 4,298,003 | 11/1981 | Theeuwes et al. | 128/260 |
| 4,320,759 | 3/1982 | Theeuwes | 128/260 |
| 4,327,725 | 5/1982 | Cortese et al. | 128/260 |
| 4,350,271 | 9/1982 | Eckenhoff | 604/892 X |
| 4,455,143 | 6/1984 | Theeuwes | 604/890 |
| 4,608,048 | 8/1986 | Cortese | 604/890 |
| 4,610,686 | 9/1986 | Ayer | 604/890 |
| 4,612,008 | 9/1986 | Wong | 604/892 |
| 4,643,731 | 2/1987 | Eckenhoff | 604/892 |

Primary Examiner—Joseph L. Schofer
Assistant Examiner—F. M. Teskin
Attorney, Agent, or Firm—Paul L. Sabatine; Edward L. Mandell; Steven F. Stone

[57] ABSTRACT

An osmotic system is disclosed comprising a wall comprising in at least a part of a semipermeable material that surrounds a compartment. The compartment contains a first osmotic composition comprising a beneficial drug selected from the group consisting of a calcium antagonist, angiotensin enzyme inhibitor and nonsteroidal anti-inflammatory drugs, and a second and different osmotic composition. A passageway in the wall connects the first composition with the exterior of the system.

79 Claims, 5 Drawing Sheets

OSMOTIC SYSTEM COMPRISING PLURALITY OF MEMBERS FOR DISPENSING DRUG

CROSS-REFERENCE TO RELATED PATENT APPLICATIONS

This patent application is a continuation-in-part of U.S. Pat. Appln. Ser. No. 06/685,687 filed on Dec. 24, 1984 now abandoned which Appln. Ser. No. 06/685,687 is a continuation-in-part of U.S. Pat. Appln. Ser. No. 06/493,760 filed May 11, 1983 now abandoned, which applications are incorporated herein by reference and benefits are claimed of their filing dates. These patent applications are assigned to the ALZA Corp., of Palo Alto, Calif.

FIELD OF THE INVENTION

This invention pertains to both a novel and unique delivery system. More particularly, the invention relates to an osmotic device comprising a wall comprising at least in part in one embodiment a polymeric material that surrounds a compartment comprising: (1) a first osmotic composition comprising a beneficial agent, and an osmopolymer and optionally an osmagent, said composition in contacting arrangement with (2) a second osmotic composition comprising an osmopolymer and optionally an osmagent. At least one passageway through the wall connects the exterior of the osmotic device with the osmotic composition containing the beneficial agent for delivering the composition comprising the beneficial agent from the osmotic device. The osmotic device is preferably useful for delivering (3) beneficial agents that because of their solubilities are difficult to deliver in a known amount at a controlled rate from an osmotic dispensing system, and for delivering (4) beneficial agents that are therapeutically very active and are dispensed in small amounts, that is in minidoses, at a controlled rate from the osmotic dispensing system.

BACKGROUND OF THE INVENTION

Since the beginning of antiquity, both pharmacy and medicine have sought a delivery system for administering a beneficial drug. The first written reference to a delivery system is in the Eber Papyrus, written about 1552 B. C. The Eber Papyrus mentions delivery systems such as anal suppositories, vaginal pessaries, ointments, oral pill formulations, and other delivery systems. About 2500 years passed without any advance in dosage form development, when the Arab physician Rhazes, 865–925 A. D., invented the coated pill. About a century later the Persian Avicenna, 980–1037 A. D., coated pills with gold or silver for increasing patient acceptability and for enhancing the effectiveness of the drug. Also round this time, the first tablet was described in Arabian manuscripts written by al-Zahrawi, 936–1009 A. D. The manuscripts described a tablet formed from the hollow impressions, in two facing tablet molds. Pharmacy and medicine waited about 800 years for the next innovation in delivery systems when, in 1883, Mothes invented the capsule for administering drug. The next quantum leap in dosage forms came in 1972 with the invention of the osmotic delivery system by inventors Theeuwes and Higuchi as disclosed in U.S. Pat. Nos. 3,845,770 and 3,916,899.

The osmotic system disclosed in those patents mentioned immediately above comprise in at least part a semipermeable wall that surrounds a compartment containing a useful agent. The wall is permeable to the passage of an external fluid, and it is substantially impermeable to the passage of useful agent. There is at least one passageway through the wall for delivering the useful agent from the osmotic system. These systems release a useful agent by fluid being imbibed through the semipermeable wall into the compartment at a rate determined by the thickness and permeability of the semipermeable wall and the osmotic pressure gradient across the semipermeable wall to produce an aqueous solution containing useful agent that is dispensed through a passageway from the system. These systems are extraordinarily effective for delivering a useful agent that is soluble in the fluid and exhibits an osmotic pressure gradient across the semipermeable wall against the external fluid.

A pioneer advancement in osmotic delivery systems, manufactured in the form of an osmotic device, was presented to the dispensing arts by inventor Felix Theeuwes in U.S. Pat. No. 4,111,202. In this patent, the delivery kinetics of the osmotic device is enhanced for delivering useful agents, including drugs, that are insoluble to very soluble in the fluid, by manufacturing the osmotic device with a useful agent compartment and an osmagent compartment separated by an internal film. The internal film is movable from a rested to an expanded state. The osmotic device delivers agent by fluid being imbibed through the semipermeable wall into the osmagent compartment producing a solution that causes the compartment to increase in volume and act as a driving force that is applied against the film. This force urges the film to expand in the device against the useful agent compartment and correspondingly diminish the volume of the useful agent compartment, whereby useful agent is dispensed through the passageway from the osmotic device. While this device operates successfully for its intended use, and while it can deliver numerous useful agents of varying solubilities, its use can be limited because of the manufacturing steps and costs needed for fabricating and placing the movable film in the compartment of the osmotic device.

In U.S. Pat. No. 4,327,725 patentees Richard Cortese and Felix Theeuwes provided an osmotic dispensing device for delivering beneficial agents, that because of their solubilities in aqueous and biological fluids, are difficult to deliver in meaningful amounts at controlled rates over time. The osmotic devices of this patent comprise a semipermeable wall surrounding a compartment containing a beneficial agent that is insoluble to very soluble in aqueous and biological fluids, and an expandable hydrogel. In operation the hydrogel expands in the presence of external fluid that is imbibed into the device thereby dispensing the beneficial agent through the passageway from the device. This device operates successfully for its intended use, and it delivers many difficult to deliver beneficial agents for their intended purpose. Now it has been observed that the value of this system can be enhanced unexpectedly by the present invention providing a composition comprising the beneficial agent and a carrier gel, which composition cooperates with an expanding gel thereby leading to improved beneficial agent administration and to improved therapy.

It will be appreciated by those versed in the dispensing art, taat if an osmotic device can be provided that exhibits a high level of osmotic activity, such an osmotic device would have a positive value and represent an advancement in the dispensing art. Likewise, it will be immediately appreciated by those versed in the dispensing art that if an osmotic device is made available possessing dual thermodynamic osmotic activity for delivering increased amounts of a beneficial agent, said osmotic device would find practical application in the fields of pharmacy and medicine.

OBJECT OF THE INVENTION

Accordingly, in view of the above presentation, it is an immediate object of this invention to provide an osmotic system that can be manufactured by standard manufacturing techniques into osmotic devices of various sizes, shapes and forms that represent a further improvement and advancement in the dispensing art.

Another object of the invention is to provide an osmotic system manufactured in the form of an osmotic device for delivering in vivo a beneficial drug that is difficult to deliver and now can be delivered by the osmotic device provided by this invention in therapeutically effective amounts over time.

Another object of the invention is to provide an osmotic system possessing dual osmotic activity that operates as an integrated unit, which system comprises a compartment containing a first osmotic composition comprising a drug, and preferably an omopolymer and/or an osmagent, and a second osmotic composition comprising an osmopolymer and an optional osmagent, with the compositions acting in concert for delivering the drug through a passageway of controlled dimensions from the osmotic device.

Yet another object of the invention is to provide an osmotic device having means for high loading of a water insoluble or a slightly water soluble beneficial agent such as a drug and means for delivering the beneficial agent in either instance at a controlled rate and continuously over time to a drug recipient.

Yet another object of the invention is to provide an osmotic device that can deliver a pH dependent beneficial agent by providing a neutral medium for delivering the beneficial agent in a finely dispersed form for increasing its surface area and for maximizing the dissolution rate of the beneficial agent.

Still yet another object of the invention is to provide an osmotic system for delivering a drug having a very low dissolution rate that is the rate limiting step for delivering the drug from the system, but now can be delivered by using an osmotic composition that functions in situ as a carrier, as a wetting agent and as a solubilizing agent for increasing the dissolution rate and the solubility of the drug, thereby enhancing its delivery from the osmotic system.

Another object of the invention is to provide an osmotic system comprising means for maintaining a high level of osmotic activity of a polymer which polymer is used for delivering a beneficial agent from the osmotic system.

Still a further object of the invention is to provide an osmotic, therapeutic device that can administer a complete pharmaceutical dosage regimen comprising poorly soluble to very soluble agents, at a controlled rate and continuously for a particular time period, the use of which requires intervention only for the initiation and possible termination of the regimen.

Still another object of this invention is to provide an osmotic system manufactured as an osmotic device, which device can house a small amount of a therapeutic agent and dispense small doses, that is minidoses, of the agent at a controlled rate to the gastrointestinal tract throughout the length of the gastrointestinal tract.

Still another object of the invention is to provide an osmotic system manufactured with a compartment housing a first polymer means and a second polymer means in contacting arrangement that simultaneously maintain their original identity and function as an integrated layered unit for delivering the beneficial drug from the osmotic system.

Still a further object of this invention is to provide an osmotic device that possesses the ability to delivery drugs over a broad range of drug delivery rates, and can deliver the drugs according to a predetermined drug release rate pattern to a biological recipient over time.

A still further object of the invention is to provide a delivery system that avoids patient compliance problems and uses less drug, thereby minimizing side effects and provides efficiency in treatment for better health.

Other objects, features, aspects and advantages of the invention will be more apparent to those versed in the dispensing art from the following detailed specification taken in conjunction with the figures and the accompanying claims.

BRIEF DESCRIPTION OF THE DRAWINGS

In the drawings, which are not drawn to scale, but are set forth to illustrate various embodiments of the invention, the drawing figures are as follows.

In the drawings and the specification, like parts in related figures are identified by reference numerals. The terms appearing earlier in the specification and in the descrption of the drawings, as well as embodiments thereof, are further detailed elsewhere in the disclosure.

DETAILED DESCRIPTION OF THE DRAWINGS

Figure 1:
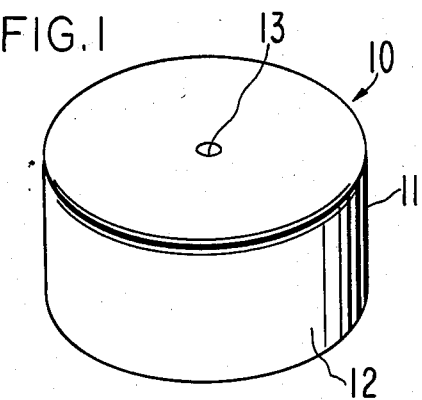
FIG. 1 is an isometric view of an osmotic device designed for orally administering a beneficial agent to the gastrointestinal tract.

Turning now to the drawings in detail, which are examples of various osmotic devices provided by the inventoon, and which examples are not to be construed as limiting, one example of an osmotic device is seen in FIG. 1. In FIG. 1, osmotic device 10 is seen comprising a body member 11 having a wall 12 and at least one passageway 13 for releasing a beneficial agent from osmotic device 10.

Figure 2:
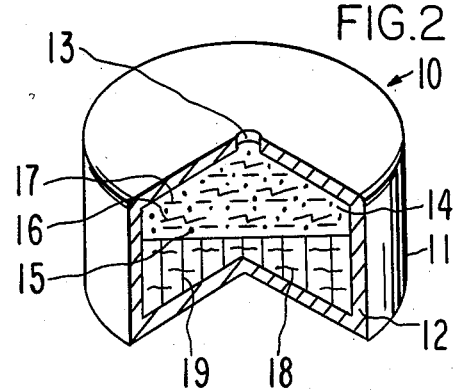
FIG. 2 is an opened view of the osmotic device of FIG. 1 illustrating the structure of the osmotic device of FIG. 1.

In FIG. 2, osmotic device 10 of FIG. 1 is seen in opened section. In FIG. 2, osmotic device 10 comprises a body 11, a wall 12 that surrounds and forms internal compartment 14, that communicates through a passageway 13 with the exterior of osmotic device 10. Wall 12 comprises totally a semipermeable composition or at least in part a semipermeable composition. When wall 12 comprises at least in part a semipermeable composition the remainder of the wall is comprised of a non-semipermeable composition. Compartment 14 contains a first osmotic composition comprising a beneficial agent 15, represented by dots, which agent 15 can be from insoluble to very soluble in fluid imbibed into compartment 14, an optional osmagent 16, represented by irregular lines, that is soluble in fluid imbibed into compartment 14 and exhibits an osmotic pressure gradient across semipermeable wall 12 against an external fluid and an osmopolymer 17, represented by horizontal dashes, that imbibes and/or absorbs fluid into compartment 14 and exhibits an osmotic pressure gradient across semipermeable wall 12 against an exterior fluid present in the environment of use. Wall 12 comprises of a semipermeable composition that is substantially permeable to the passage of the exterior fluid, and it is substantially impermeable to the passage of agent 15, osmagent 16 and osmopolymer 17. Semipermeable wall 12 is non-toxic and it maintains its physical and chemical integrity during the delivery life of agent 15 from device 10.

Compartment 14 also houses a second osmotic composition that is distant from passageway 13 and in contacting relation with the first composition. The second composition contributes an expandable driving force that acts in cooperation with the first osmotic composition for delivering the maximum amount of beneficial agent 15 from osmotic device 10. The second osmotic composition comprises an optional osmagent 18, represented by wavy lines, that is soluble in fluid imbibed into compartment 14 and exhibits an osmotic pressure gradient across semipermeable wall 12 against an external fluid, blended with a presently preferred osmopolymer 19, represented by vertical lines, that imbibes fluid into compartment 14 and exhibits an osmotic pressure gradient across semipermeable wall 12 against external fluid. Osmopolymer 17 and osmopolymer 19 are hydrophilic water soluble or lightly cross-linked water soluble polymers, and they possess osmotic properties such as the ability to imbibe external fluid through the semipermeable wall, exhibit an osmotic pressure gradient across the semipermeable wall against the external fluid, and swell or expand in the presence of the fluid in the compartment. Osmopolymers 17 and 19 preferably are mixed with osmagent 16 and 18, respectively, for imbibing the optimal maximum volume of external fluid into compartment 14. This imbibed fluid is available to osmopolymers 17 and 19 to optimize the volumetric rate and for total expansion of osmopolymer 17 and 19. That is, osmopolymers 17 and 19 absorb fluid imbibed into compartment 14 by the osmotic imbibition action of osmopolymers 17 and 19 supplemented by the osmotic imbibition action of osmagents 16 and 18 for effecting the optimal maximum expansion of osmopolymers 17 and 19 from a rested to an enlarged, that is, an expanded state.

In operation, the delivery of beneficial agent 15 from osmotic device 10 is carried out, in one presently preferred embodiment, by (1) imbibition of fluid by the first composition to form a fluidic composition in situ and delivery of the suspension through the passageway; and concurrently by (2) imbibition of fluid by the second composition causing the second composition to swell and cooperate with the first composition for driving the agent suspension through at least one or more than one passageways. According to the operation described, the osmotic device may be considered as a cylinder, with the second composition expanding like the movement of a piston for aiding in delivering the agent composition from the osmotic device. For the purpose of the present analysis, the volume rate delivered by the osmotic device $F_t$ is composed of two sources; the water imbibition rate by the first composition F, and the water imbibition rate by the second composition Q wherein:

$$F_t = F + Q \tag{1}$$

Since the boundary between the first composition and the second composition hydrates very little during the functioning of the osmotic device, there is insignificant water migration between the compositions. Thus, the water imbibition rate of the second composition, Q, equals the expansion of its volume:

$$\frac{dv_p}{dt} = Q \tag{2}$$

The total delivery rate from the osmotic device is then, $$\frac{dm}{dt} = F_t \cdot C = (F + Q)C \tag{3}$$

wherein C is the concentration of beneficial agent in the delivered slurry or solution. Conservation of the osmotic device volume, V, and the surface area, A, gives equations (4) and (5):

$$V = V_d + V_p \tag{4}$$

$$A = A_d + A_p \tag{5}$$

wherein $V_d$ and $V_p$ equal the volumes of the first composition and the second composition, respectively; and wherein $A_d$ and $A_p$ equal the surface area in contact with the wall by the first composition and the second composition, respectively. In operation, both $V_p$ and $A_p$ increase with time, while $V_d$ and $A_d$ decrease with timeas the device delivers beneficial agent.

The volume of the second composition that expands with time when fluid isimbibed into the compartment is given by equation (6):

$$V_p = f\left(\frac{W_H}{W_p}\right) \qquad (6)$$

wherein $W_H$ is the weight of fluid imbibed by the second composition, $W_p$ is the weight of the second composition initially present in the device, $W_H/W_p$ is the ratio of fluid to initial solid of the second composition, and $$V_p = \left(1 + \frac{W_H}{W_p}\right)\frac{W_p}{\rho} \qquad (7)$$

wherein $\rho$ is the density of the second composition corresponding to $W_H/W_p$. Thus, based on the geometery of a cyulinder, where r is the radius of the cylinder, the area of imbition is related to the volume of the swollen second composition as follows:

$$A_p = \pi r^2 + \frac{2}{r}\frac{W_p}{\rho}(1 + W_H/W_p) \qquad (8)$$

$$A_d = A - A_p \qquad (9)$$

The fluid imbibition rates into each composition are:

$$F = \left(\frac{k}{h}\right)(A_d \cdot \Delta \pi_d) \qquad (10)$$

$$Q = \left(\frac{k}{h}\right)(A_p \cdot \Delta \pi_p) \qquad (11)$$

wherein k equals the osmotic permeability of the wall, h equals the wall thickness, $\Delta \pi_d$ and $\Delta \pi_p$ are the osmotic gradients for the first composition and the second composition respectively. The total delivery rate, therefore, is (12):

$$\frac{dm}{dt} = \qquad (12)$$

$$\frac{k}{h} C \left\{ \left[A - \pi r^2 - \frac{2}{r}\frac{W_p}{\rho}(1 + W_H/W_p)\right]\Delta \pi_d + \left[\pi r^2 + \frac{2}{r}\frac{W_p}{\rho}(1 + W_H/W_p)\right]\Delta \pi_p \right\}$$

Figure 3:
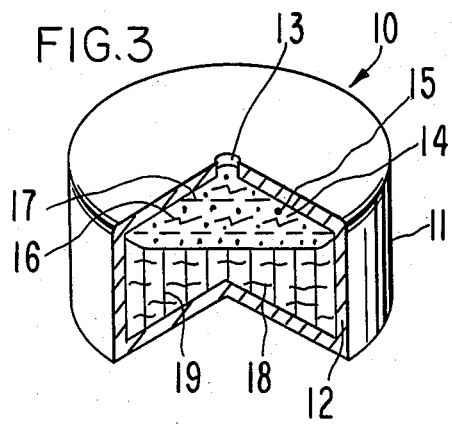
FIG. 3 is an opened view of the osmotic device of FIG. 1 illustrating the osmotic device in operation and delivering a beneficial agent from the osmotic device.
Figure 4:
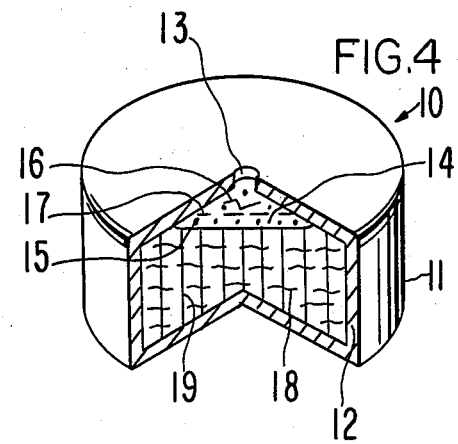
FIG. 4 is an opened view of the osmotic device of FIG. 1 considered with FIG. 3 illustrating the osmotic device in operation and comprising more than one passageway for delivering a major amount of a beneficial agent from the osmotic device.

FIGS. 3 and 4 illustrate the osmotic device in operation as described for FIGS. 1 and 2. In FIGS. 3 and 4, for osmotic device 10, fluid is imbibed by the first composition at a rate determined by the permeability of the wall and the osmotic pressure gradient across the wall. The imbibed fluid continuously forms a solution containing beneficial agent, or a suspension, or a gel comprising an osmagent and osmopolymer containing beneficial agent in suspension, which solution or suspension in either operation is released by the combined operations of device 10. These operations include the solution, or the suspension being osmotically delivered through the passageway due to the continuous formation of solution or suspension, and by the swelling and increasing volume of the different second composition, represented by the increase in height of the vertical lines in FIG. 3 and 4. This latter swelling and increase in volume applies pressure against the solution or suspension thereby aiding the first composition and simultaneously causing delivery of beneficial agent through the osmotic passageway to the exterior of the device. The device can comprise more than one passageway, a microporous insert, or pores formed by leaching a leachable pore-former thereby providing pore-passageways for releasing drug to the exterior of the device. Thus, the osmotic device provided by this invention can be viewed as a single unit construction device comprising two compositions containing two polymeric structures acting in concert for effective drug administration to a patient.

The first composition and the second composition act together to substantially insure that delivery of beneficial agent from the compartment is controlled and constant over a prolonged period of time by two methods. First, the first composition imbibes external fluid across the wall, thereby forming either a solution or a suspension, which is substantially delivered at non-zero order, without the second composition present, since the driving force decays with time. Second, the second composition operates by two simultaneous operations: (1) the second composition operates to continuously concentrate beneficial agent by imbibing some fluid from the first composition to help keep the concentration of beneficial agent from falling below saturation and, (2) the second composition operating by imbibing external fluid across the wall continuously and, consequently, increases in volume, thereby exerting a force against the first composition and diminishing the volume of beneficial agent first composition, thusly directing beneficial agent to the passageway in the compartment. Additionally, as the extra solution or suspension formed in the first composition is squeezed out, that is, delivered from device 10, the osmotic composition closely contacts the internal wall and generates a constant osmotic pressure and, therefore, a constant delivery rate in conjunction with the second composition. The swelling and expansion of the second composition, with its accompanying increase in volume, along with the simultaneous corresponding reduction in volume of the first composition assures the delivery of beneficial agent through the osmotic passageway at a controlled rate over time.

Device 10 of FIGS. 1 through 4 can be made into many embodiments including the presently preferred embodiments for oral use; for releasing either a locally or systemically acting therapeutic agent in a gastrointestinal tract. Oral system 10 can have various conventional shapes and sizes, such as round with a diameter of 3/16 inches to ⅝ inches. In these forms system 10 can be adapted for administering beneficial agent to numerous animals, including warm blooded animals, humans, avians, reptiles and pisces.

Figure 5:
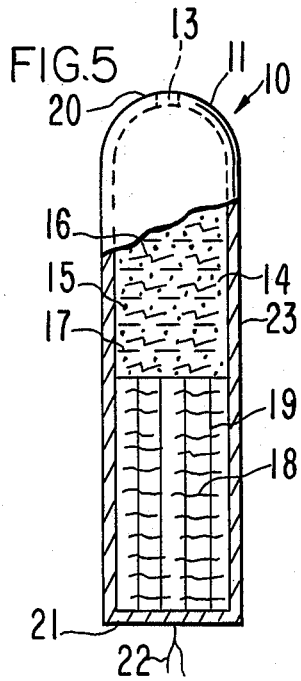
FIG. 5 shows an osmotic therapeutic device with its wall partially broken away, designed for delivering a beneficial agent into a body passageway, such as the ano-rectal and vaginal passageways.
Figure 6:
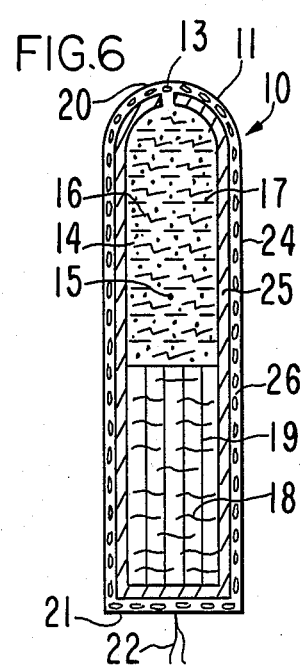
FIG. 6 shows the osmotic device of FIG. 5 with a different wall structure.
Figure 7:
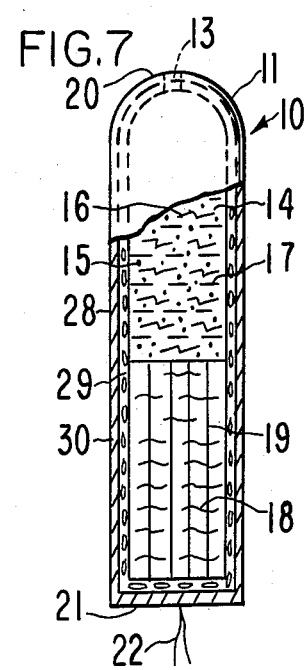
FIG. 7 shows the osmotic device of FIG. 5 depicting a different wall structure than the wall structure depicted in FIG. 6.

FIGS. 5, 6 and 7 show another embodiment provided by this invention. FIGS. 5, 6 and 7 show an osmotic device 10 designed for placement in a body passageway, such as a vagina, or the ano-rectal canal. Device 10 has an elongated, cylindrical, self-sustaining shape with a curved lead end 20, a trailing end 21, and it is optionally equipped with manually controlled strings 22 for easily removing device 10 from the biological passageway. Device 10 is structurally identical with the device described above in FIGS. 1 through 4, and it operates in a like manner. In FIG. 5, device 10 is depicted with a semipermeable wall 23, in FIG. 6 with a laminated wall 24 comprising an inner semipermeable lamina 25 adjacent to compartment 14 and an external microporous lamina 26 distant from compartment 14. Microporous lamina 26 can have preformed pores, or its pores can be formed when device 10 is in the environment of use, such as by leaching a leachable material from the lamina. The pores of lamina 26 are of controlled porosity size and they can function as pore-passageways for the release of beneficial agent 15 from device 10. In FIG. 6, a pore-passageway and a laser-passageway function as the composite passageway 13 for releasing agent 15 from device 10. In FIG. 7, device 10 comprises a laminated wall 28 formed of a microporous lamina 29 next to compartment 14, and a semipermeable lamina 30 facing the environment of use and in laminar arrangement with microporous lamina 29. The semipermeable lamina used for manufacturing these osmotic devices is permselective since it is permeable to the passage of fluid and substantially impermeable to the passage of agent, osmagent and osmopolymer. The micropores of lamina 29 can align with the passageway of lamina 30 for releasing drug from device 10. Device 10 delivers a beneficial agent for absorption by the vaginal mucosa, or the ano-rectal mucosa, to produce an in vivo local or systemic effect over a prolonged period of time.

In this construction of osmotic systems of this invention, it has been found that the polymeric membranes used to regulate the entry of fluids such as water from the exterior to the interior of the system can be microporous as well as semipermeable. The osmotic system functions by retaining the osmopolymers during operation within the microporous polymer wall due to the high viscosity of the osmopolymers. When the osmopolymers are selected to have swelling characteristics independent of pH of the environment of use the release rate of such a system will be pH indepenqent.

The osmotic devices of FIGS. 1 through 7 can be used for delivering numerous agents including drugs at a controlled rate independent of the drug pH dependency, or where the dissolution rate of the agent can vary between low and high in fluid environments, such as gastric fluid and intestinal fluid. The osmotic devices also provide for low/high loading of agents of low solubility and their delivery at meaningful, therapeutic amounts. While FIGS. 1 through 7 are illustrative of various osmotic devices that can be made according to the invention, it is to be understood these devices are not to be construed as limiting, as the devices can take a wide variety of shapes, sizes and forms adapted for delivering beneficial agents to the environment of use. For example, the devices include buccal, implant, artificial gland, cervical, intrauterine, ear, nose, dermal, vaginal, percutaneous, subcutaneous, and like delivery devices. The devices also can be sized, shaped, structured and adapted for delivering an active agent in streams, aquariums, fields, factories, reservoirs, laboratory facilities, hot houses, transportation means, naval means, military means, hospitals, veterinary clinics, nursing homes, farms, zoos, sickrooms, chemical reactions, and other environments of use.

DETAILED DESCRIPTION OF THE INVENTION

In accordance with the practice of this invention it has now been found that osmotic delivery device 10 can be manufactured with a first osmotic composition and a different second osmotic composition mutually housed in cooperative relationship in the compartment of the device. The compartment is formed by a wall comprising a material that does not adversely affect the beneficial agent, osmagent, osmopolymer, and the like. The wall is permeable, that is the wall is permeable to the passage of an external fluid such as water and biological fluids, and it is substantially impermeable to the passage of agents, osmagents, osmopolymers, and the like. The wall comprises a material that does not adversely affect an animal, or host, or the components comprising the device, and the selectively semipermeable materials used for forming the wall are non-erodible and they are insoluble in fluids. Typical materials for forming the wall are in one embodiment cellulose esters, cellulose ethers and cellulose esterethers. These cellulosic polymers have a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, mono-, di- and tricellulose alkanylates, mono-, di- and tricellulose aroylates, and the like. Exemplary polymers include cellulose acetate having a D.S. up to 1 and an acetyl content up to 21%; cellulose acetate having an acetyl content of 32 to 39.8%; cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers include cellulose propionate having a D.S. of 1.8 and a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, co-esters of cellulose such as cellulose acetate butyrate and cellulose acetate propionate, and the like.

Additional polymers include ethyl cellulose of various degree of etherification with ethoxy content of from 40% to 55%, acetaldehyde dimethyl cellulose acetate, cellulose acetate ethyl carbamate, cellulose acetate methyl carbamate, cellulose acetate diethyl aminoacetate, semipermeable polyamides; semipermeable polyurethanes; semipermeable sulfonated polystyrenes; semipermeable cross-linked selective polymers formed by the coprecipitation of a polyanion and a polycation as disclosed in U.S. Pat. Nos. 3,173,876; 3,276,586; 3,541,005; 3,541,006, and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); semipermeable cross-linked poly(vinylbenzyltrimethyl ammonium chloride); semipermeable polymers exhibiting a fluid permeability of $2.5 \times 10^{-8}$ to $2.5 \times 10^{-4}$ (cm$^2$/hr·atm) expressed per atmosphere of hydrostatic or osmotic pressure difference across the semipermeable wall. The polymers are known to the art in U.S. Pat. Nos. 3,845,770; 3,916,899; and 4,160,020; and in *Handbook of Common Polymers* by Scott, J. R. and Roff, W. J., 1971, published by CRC Press, Cleveland, OH.

The laminated wall comprising a semipermeable lamina and a microporous lamina are in laminar arrangement and they act in concert to form an integral laminated wall that maintains its physical and chemical integrity and does not separate into the original lamina throughout the operative agent release history of the osmotic device. The semipermeable lamina is made from the semipermeable polymeric materials, the semipermeable homopolymers, and the semipermeable copolymers presented above, and the like.

Microporous lamina suitable for manufacturing a wall or a laminated osmotic device generally comprises preformed microporous polymeric materials, and polymeric materials that can form a microporous lamina in the environment of use. The microporous materials in both embodiments are laminated to form the laminated wall. The preformed materials suitable for forming the microporous lamina are essentially inert, they maintain their physical and chemical integrity during the period of agent release and they can be described generically as having a sponge like appearance that provides a supporting structure for a semipermeable lamina and also provides a supporting structure for microscopic sized interconnected pores or voids. The microporous materials can be isotropic wherein the structure is homogeneous through out a cross sectional area, or they can be anisotropic wherein the structure is non-homogeneous throughout a cross sectional area. The pores can be continuous pores that have an opening on both faces of a microporous lamina, pores interconnected through tortuous paths of regular and irregular shapes, including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and the number of pores. The pore size of a microporous lamina is easily ascertained by measuring the observed pore diameter at the surface of the material under the electron microscope. Generally, materials possessing from 5% to 95% pores and having a pore size of from 10 angstroms to 100 microns can be used for making a microporous lamina.

The pore size and other parameters characterizing the microporous structure also can be obtained from flow measurements, where a liquid flux, J, is produced by a pressure difference $\Delta P$, across the lamina. The liquid flux through a lamina with pores of uniform radius extended through the lamina and perpendicular to its surface with area A given by relation (13):

$$J = \frac{N\pi r^4 \Delta P}{8\eta \Delta x} \quad (13)$$

wherein J is the volume transported per unit time and lamina area containing N number of pores of radius r, $\eta$ is the viscosity of the liquid and $\Delta P$ is the pressure difference across the lamina with thickness $\Delta x$. For this type of lamina, the number of pores N can be calculated from relation (14), wherein $\epsilon$ is the porosity defined as the ratio of void volume to total volume of the lamina; and A is the cross sectional area of the lamina containing N pores.

$$N = \frac{\epsilon A}{\pi r^2} \quad (14)$$

The pore radius then is calculated from relation (15):

$$r = \left[ 8\eta \frac{\Delta x \cdot \tau}{\Delta P \cdot \epsilon} J' \right]^{\frac{1}{2}} \quad (15)$$

wherein J' is the volume flux through the lamina per unit area produced by the pressure difference $\Delta P$ across the lamina, $\eta$, $\epsilon$ and $\Delta x$ have the meaning defined above and $\tau$ is the tortuosity defined as the ratio of the diffusional path length in the lamina to the lamina thickness. Relations of the above type are discussed in *Transport Phenomena In Membranes*, by Lakshminatayanaiah, N. Chapter 6, 1969, published by Academic Press, Inc., New York.

As discussed in this reference, supra, on page 336, in Table 6.13, the porosity of the lamina having pores with radius r can be expressed relative to the size of the transported molecule having a radius a, and as the ratio of molecular radius to pore radius a/r decreases, the lamina becomes porous with respect to this molecule. That is, when the ratio a/r is less than 0.3, the lamina becomes substantially microporous as expressed by the osmotic reflection coefficient $\sigma$ which decreases below 0.5. Microporous lamina with a reflection coefficient $\sigma$ in the range of less than 1, usually from 0 to 0.5, and preferably less than 0.1 with respect to the active agent are suitable for fabricating the system. The reflection coefficient is determined by shaping the material in the form of a lamina and carrying out water flux measurements as a function of hydrostatic pressure difference and as a function of the osmotic pressure difference caused by the active agent. The osmotic pressure difference creates a hydrostatic volume flux, and the reflection coefficient is expressed by relation (16):

$$\sigma = \frac{\text{osmotic volume flux}}{\text{hydrostatic volume flux}} \quad (16)$$

Properties of microporous materials are described in *Science*, Vol. 170, pp 1302–1305, 1970; *Nature*, Vol. 214, page 285, 1967; *Polymer Engineering and Science*, Vol. 11, pp 284–288, 1971; U.S. Pat. Nos. 3,567,809 and 3,751,536; and in *Industrial Processing With Membranes*, by Lacey, R. E., and Loeb, Sidney, pp 131–134, 1972.

Microporous materials having a preformed structure are commercially available and they can be made by art known methods. The microporous materials can be made by etching, nuclear tracking, by cooling a solution of flowable polymer below the freezing point whereby solvent evaporates from the solution in the form of crystals dispersed in the polymer and then curing the polymer followed by removing the solvent crystals, by cold or hot stretching at low or high temperatures until pores are formed, by leaching from a polymer a soluble component by an appropriate solvent, by ion exchange reaction, and by polyelectrolyte process. Process for repairing microporous materials are described in *Synthetic Polymer Membranes*, by R. E. Kesting, 1971, Chapters 4 and 5, published by McGraw Hill, Inc; *Chemical Reviews*, "Ultrafiltration", Vol. 18, pp 373 to 455, 1934; *Polymer Eng. and Sci.*, Vol. 11. No. 4, pp 284–288, 1971; *J. Appl. Poly. Sci.*, 1971, Vol. 15, pp 811-829, 1971; and in U.S. Pat. Nos. 3,565,259; 3,615,024; 3,751,536; 3,801,692; 3,852,224, and 3,849,528.

Microporous materials useful for making the wall or the lamina include microporous polycarbonates comprised of linear polyesters of carbonic acid in which carbonate groups recur in the polymer chain; microporous materials prepared by the phosgenation of a dihydroxyl aromatic, such as bisphenol A; microporous poly(vinyl chloride); microporous polyamides such as polyhexamethylene adipamide; microporous modacrylic copolymers including those formed from 60% vinyl chloride and 40% acrylonitrile; styrene acrylic copolymers; porous polysulfones characterized by diphenylene sulfone groups in a linear chain thereof; poly(vinylidene) halides; polychloroethers; acetal polymers; polyesters prepared by esterification of a dicarboxylic acid or anhydride with an alkylene polyol; poly(alkylenesulfides); phenolic polyesters; microporous poly(saccharides); microporous polymers having substituted and unsubstituted anhydroglucose units exhibiting a higher permeability to the passage of water and biological fluids than a semipermeable lamina; asymmetric porous polymers; cross linked olefin polymers; hydrophobic or hydrophilic microporous homopolymers, copolymers or interpolymers having a reduced bulk density; and materials described in U.S. Pat. Nos. 3,597,752; 3,643,178; 3,654,066; 3,709,774; 3,718,532; 3,803,061; 3,852,224; 3,853,601; and 3,852,388, in British Patent No. 1,126,849, and in Chem. Abst., Vol. 71 4274F, 22572F, 22573F, 1969.

Additional microporous materials include microporous poly(urethanes); microporous cross linked, chain extended poly(urethanes); microporous poly(urethanes) in U.S. Pat. No. 3,524,753; microporous poly(imides); microporous poly(benzimidazoles); regenerated microporous proteins; semi-solid cross linked microporous poly(vinylpyrrolidone); microporous materials prepared by diffusion of multivalent cations into polyelectrolyte sols as in U.S. Pat. No. 3,565,259; anisotropic microporous materials of ionically associated polyelectrolytes; porous polymers formed by the coprecipitation of a polycation and a polyanion as described in U.S. Pat. Nos. 3,276,589; 3,541,055; 3,541,066 and 3,546,142; derivatives of poly(styrene), such as microporous poly(-sodium styrenesulfonate) and microporous poly(vinyl benzyltrimethyl-ammonium chloride), the microporous materials disclosed in U.S. Pat. Nos. 3,615,024, 3,646,178, 3,852,224, and the like.

Further, the micropore forming material used for the purpose of the invention includes the embodiment wherein the microporous wall or the lamina is formed in situ by a pore former being removed by dissolving, extracting, eroding, or leaching it to form the microporous lamina during the operation of the system. The pore former can be a solid or a liquid. The term "liquid", for this invention, embraces semi-solids and viscous fluids. The pore formers can be inorganic or organic. The pore formers suitable for the invention include pore formers that can be extracted, dissolved or leached without any chemical change in the polymer. The pore forming solids have a size of about 0.1 to 200 micrometers and they include alkali metal salts such as sodium chloride, sodium bromide, potassium chloride, potassium sulfate, potassium phosphate, sodium benzoate, sodium acetate, sodium citrate, potassium nitrate, and the like. The alkali earth metal salts include calcium phosphate, calcium nitrate, and the like. The transition metal salts include ferric chloride, ferrous sulfate, zinc sulfate, cupric chloride, manganese fluoride, manganese fluorosilicate, and the like. The pore formers include organic compounds such as polysaccharides. The polysaccharides include the sugars: sucrose, glucose, fructose, mannose, galactose, aldohexose, altrose, talose, lactose, monosaccharides and disaccharides; and polyalcohols such as mannitol and sorbitol. Also, organic aliphatic and aromatic oils and solids, including diols and polyols, as exemplified by polyhydric alcohols, poly(alkylene glycols), polyglycols, alkylene glycols, poly(alpha-omega)-alkylenediols esters or alkylene glycols and the like; water soluble cellulosic polymers such as hydroxyloweralkyl cellulose, hydroxypropyl methylcellulose, methyl cellulose, methylethyl cellulose, hydroxyethyl cellulose and the like; water soluble polymers such as polyvinylpyrrolidone, sodium carboxymethylcellulose and the like. The pore-formers on their removal from the lamina form channels through the lamina. These can serve as pore-passageways for effective release of agent from the system. In a preferred embodiment the non-toxic, pore forming agents are selected from the group consisting of inorganic and organic salts, carbohydrates, polyalkylene glycols, poly(alpha-omega)-alkylenediols, esters of alkylene glycols, glycols, alcohols, hydric alcohols, and water soluble polymers used for forming a microporous lamina in a biological environment. Generally, for the purpose of this invention, when the polymer forming the microporous lamina contains more than 15% by weight of a pore former, the polymer is a precursor microporous lamina that on removing the pore former yields a lamina which is substantially microporous.

The expression "passageway" as used herein comprises means and methods suitable for releasing the agent or drug from the osmotic system. The expression includes aperture, orifice, hole, porous element, hollow fiber, capillary tube, microporous insert, pore, microporous overlay, or bore, and the like, through the semipermeable lamina, the microporous lamina, or through the laminated wall. The passageway can be formed by mechanical drilling, laser drilling, eroding an erodible element, extracting, dissolving, bursting or leaching a passageway-former from the wall. One description of a passageway and the maximum and minimum dimensions for a passageway, are disclosed in U.S. Pat. Nos. 3,845,770 and 3,916,899. The osmotically calibrated passageway has a maximum cross-sectional area, $A_s$, defined by the relation (17) as follows:

$$A_{s\ (max)} = \frac{L}{F} \times \frac{Q_p}{t} \times \frac{1}{DS} \tag{17}$$

wherein L is the length of the passageway $Q_p/t$ is the mass delivery rate of the agent, D is the diffusion coefficient of the agent, S is the solubility of the agent in the fluid, and F is from 2 to 1000, said passageway having a minimum area $A_s$ defined by relation (18) as follows:

$$A_{s\ (min)} = \left[ \frac{Lv}{t} \times 8 \times \frac{\pi\eta}{\Delta P} \right]^{\frac{1}{2}} \tag{18}$$

wherein L is the length of the passageway, $v/t$ is the agent solution volume delivery rate, $\pi$ is 3.14; $\sigma$ is the viscosity of agent solution dispensed from the device and $\Delta P$ is the hydrostatic pressure difference between the inside and the outside of the compartment having a value up to 20 atmospheres.

In addition, one or more passageways can be introduced into the system. The number of passageways N can be large, but should satisfy the condition that the delivery rate is substantially governed by the imbibition flux of water across the surrounding membrane.

The passageway can be a pore formed by leaching sorbitol and the like from a wall, as disclosed in U.S. Pat. No. 4,200,098. This patent discloses pores of controlled size-porosity formed by dissolving, extracting or leaching a material from a wall, such as sorbitol from cellulose acetate. The pore-passageways extend from the inside to the outside of the wall for effective release of beneficial agent including a drug to the exterior of the system. U.S. Pat. No. 4,285,987 discloses an osmotic system comprising a first osmotic device comprising a cellulose acetate wall comprising leachable sorbitol for forming a pore for releasing osmotically active potassium chloride from an osmotic core. The first device that released drug through a laser drilled passageway. This patent discloses a device that comprises drug released through a pore-passageway and a laser passageway within the total structure of the same device.

The osmotically effective compounds that can be used for the purpose of this invention include inorganic and organic compounds that exhibit an osmotic pressure gradient across a semipermeable wall, or across a microporous, or a laminated wall, against an external fluid. The osmotically effective compounds, along with the osmopolymers, imbibe fluid into the osmotic device thereby making available in situ fluid for imbibition and/or absorption by an osmopolymer to enhance its expansion, and/or for forming a solution or suspension containing a beneficial agent for its delivery through a passageway form the osmotic device.

The osmotically effective compounds are known also as osmotically effective solutes, and also as osmagents. The osmotically effective compounds are used by mixing them with a beneficial agent, or with an osmopolymer for forming a solution, or suspension containing the beneficial agent that is osmotically delivered from the device. The expression limited solubility as used herein means the agent has a solubility of about less than 5% by weight in the aqueous fluid present in the environment. The osmotic solutes are used by homogeneously or heterogeneously mixing the solute with the agent or osmopolymer and then charging them into the reservoir. The solutes and osmopolymers attract fluid into the reservoir producing a solution of solute in a gel which is delivered from the system concomitantly transporting undissolved and dissolved beneficial agent to the exterior of the system. Osmotically effective solutes used for the former purpose include magnesium sulfate, magnesium chloride, potassium sulfate, sodium sulfate, lithium sulfate, potassium acid phosphate, d-mannitol, urea, inositol, magnesium succinate, tartaric acid, carbohydrates such as raffinose, sucrose, glucose, alpha-d-lactose monohydrate, sorbitol, and mixtures thereof. The amount of osmagent in the compartment will generally be from 0.01% to 30% or higher in the first composition, and usually from 0.01% to 40% or higher in the second composition.

The osmotic solute is preferably initially present in excess and it can be in any physical form that is compatible with the beneficial agent, the device, and the osmopolymer. The osmotic pressure of saturated solutions of various osmotically effective compounds and for mixtures of compounds at 37° C., in water, are listed in Table 1. In the table, the osmotic pressure $\pi$, is in atmospheres, atm. The osmotic pressure is measured in a commercially available osmometer that measures the vapor pressure difference between pure water and the solution to be analyzed and, according to standard thermodynamic principles, the vapor pressure ratio is converted into osmotic pressure difference. In Table 1, osmotic pressures of from 20 atm to 500 atm are set forth. Of course, the invention includes the use of lower osmotic pressures from zero, and higher osmotic pressures than those set forth by way of example in Table 1. The osmometer used for the present measurements is identified as Model 320B, Vapor Pressure Osmometer, manufactured by the Hewlett Packard Co., Avondale, PA.

TABLE 1

| COMPOUND OR MIXTURE | OSMOTIC PRESSURE ATM |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Manitol-Sucrose | 170 |
| Dextrose | 82 |
| Potassium Sulfate | 39 |
| Mannitol | 38 |
| Sodium Phosphate Tribasic 12 $H_2O$ | 36 |
| Sodium Phosphate Dibasic 7 $H_2O$ | 31 |
| Sodium Phosphate Dibasic 12 $H_2O$ | 31 |
| Sodium Phosphate Dibasic Anhydrous | 29 |
| Sodium Phosphate Monobasic $H_2O$ | 28 |

The osmopolymers suitable for forming the first osmotic composition, and also suitable for forming the second osmotic composition, are osmopolymers that exhibit fluid imbibition properties. The osmopolymers are swellable, hydrophilic polymers which osmopolymers interact with water and aqueous biological fluids and swell or expand to an equilibrium state. The osmopolymers exhibit the ability to swell in water and retain a significant portion of the imbibed water within the polymer structure. The osmopolymers swell or expand to a very high degree, usually exhibiting a 2 to 50 fold volume increase. The osmopolymers can be noncross-linked or cross-linked. The swellable, hydrophilic polymers are in one presently preferred embodiment lightly cross-linked, such cross-links being formed by covalent or ionic bonds or residue crystalline regions after swelling. The osmopolymers can be of plant, animal or synthetic origin. The osmopolymers are hydrophilic polymers. Hydrophilic polymers suitable for the present purpose include poly(hydroxy-alkyl methacrylate) having a molecular weight of from 30,000 to 5,000,000; poly(vinylpyrrolidone) having molecular weight of from 10,000 to 360,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose, cross-linked agar and carboxymethyl cellulose; a mixture of hydroxypropyl methylcellulose and sodium carboxymethylcellulose, hydroxypropyl methylcellulose and sodium carboxymethyl cellulose; a water insoluble, water swellable copolymer reduced by forming a dispersion of finely divided copolymer of maleic anhydride with styrene, ethylene, propylene, butylene or isobutylene cross-linked with from 0.001 to about 0.5 moles of saturated cross-linking agent per mole of maleic anhydride in copolymer; water swellable polymers of N-vinyl lactams; polyoxyethylene-polyoxypropylene gel; polyoxybutylene-polyethylene block copolymer gel; carob gum, polyacrylic gel; polyester gel; polyurea gel; polyether gel; polyamide gel; polyimide gel; polypeptide gel; polyamino acid gel; polycellulosic gel; polygum gel; initially dry hydrogels that generally imbibe and absorb water which penetrates the glassy hydrogel and lowers its glass transition temperature; and the like.

Other osmopolymers include polymers that form hydrogels such as Carbopol ® acidic carboxy polymers, a polymer of acrylic acid cross-linked with a polyallyl sucrose, also known as carboxypolymethylene and carboxyvinyl polymer having a molecular weight of 250,000 to 4,000,000; Cyanamer ® polyacrylamides; cross-linked water swellable indene-maleic anhydride polymers; Good-rite ® polyacrylic acid having a molecular weight of 80,000 to 200,000; Polyox ® polyethylene oxide polymers having a molecular weight of 100,000 to 5,000,000 and higher; starch graft copolymers; Aqua-Keeps ® acrylate polymer polysaccharides composed of condensed glucose units such as diester cross-linked polyglucan; and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels; and in *Handbook of Common Polymers*, by Scott and Roff, published by the Chemical Rubber Company, Cleveland, OH. The amount of osmopolymer in the first osmotic composition is about 0.01 to 99%, and the amount of osmopolymer in the second osmotic composition is 5 to 100%, with the total weight of all ingredients in a composition equal to 100%. In a presently preferred embodiment, the osmopolymer identified as $P_1$ comprising the first composition is different than the osmopolymer identified as $P_2$ comprising the second composition. The osmopolymer in the first composition can be structurally different than the osmopolymer in the second composition. Or, the osmopolymer's molecular weight of the osmopolymer in the second osmotic composition is larger than the molecular weight of the osmopolymer in the first composition. The osmopolymer $P_1$ comprising the first composition serves as a pharmaceutically acceptable carrier for the active agent and it also contributes to the driving force that cooperates with osmopolymer $P_2$ comprising the second composition that delivers the agent through the passageway from the device. During operation of the device fluid is imbibed into the device resulting in the viscosity of $P_2$ being greater than the viscosity of $P_1$ In this operation $P_1$ and $P_2$ operate as a single unit substantially free of a void between their interfaced contacting surfaces of osmopolymer $P_1$ and $P_2$ for successful delivery of the beneficial agent from the osmotic device.

Osmopolymer fluid imbibition determination for a chosen polymer can be made by following the procedure described below. A round die having an inner diameter of ½ inch, fitted with a ½ inch diameter stainless steel plug, is charged with a known quantity of polymer with the plugs extending out either end. The plugs and the die were placed in a Carver press with plates between 200° F. and 300° F. A pressure of 10,000 to 15,000 PSI was applied to the plugs. After 10 to 20 minutes of heat and pressure the electrical heating to the plates was turned off, and tap water circulated through the plates. The resulting ½ inch disks were placed in an air suspension coater charged with 1.8 kg saccharide cores, placebo cores, made of any sugar such as lactose, and so forth, and coated with cellulose acetate having an acetyl content of 39.8% dissolved in 94:6 w/w, $CH_2Cl_2/CH_3OH$, to yield a 3% w/w solution. The coated systems were dried overnight at 50° C. The coated disks were immersed in water at 37° C. and periodically removed for a gravimetric determination of water imbibed. The initial imbibition pressure was calculated by using the water transmission constant for the cellulose acetate, after normalizing imbibition values for membrane surface area and thickness. The polymer used in this determination was the sodium derivative of Carbopol-934 ® polymer, prepared according to the procedure of B. F. Goodrich Service Bulletin GC-36, "Carbopol ® Water-Soluble Resins", page 5, published by B. F. Goodrich, Akron, OH.

The cumulative weight gain values, y, as a function of time, t, for the water soluble polymer disk coated with the cellulose acetate were used to determine the equation of the line $y = c + bt + at^2$ passing through those points by at least square fitting technique.

The weight gain for the Na Carbopol-934 ® is given by the equation (19) that follows: Weight gain equals $0.359 + 0.665t 0.00106t^2$ wherein t is elapsed time in minutes. The rate of water flux at any time will be equal to the slope of the line that is given by the following equations (19) and (20):

$$\frac{dy}{dt} = \frac{d(0.359 + 0.665t - 0.00206t^2)}{dt} \qquad (19)$$

$$\frac{dy}{dt} = 0.665 - 0.00412t \qquad (20)$$

To determine the initial rate of water flux the derivative is evaluated at $t=0$, and $dy/dt = 0.665 \, \mu l/min.$, which is equal to the coefficient b. Then, normalizing the imbibition rate for time, membrane surface area and thickness, and the membrane permeability constant to water, $K\pi$ may be determined according to the following equation (21):

$$K\pi = \qquad (21)$$

$$0.665 \, \mu l/min \times \left(\frac{60 \, min}{hr}\right) \times \left(\frac{1 \, ml}{1000 \, \mu l}\right)\left(\frac{0.008 \, cm}{2.86 \, cm^2}\right)$$

with $K\pi = 1.13 \times 10^{-4} \, cm^2/hr$. The $\pi$ value for NaCl was determined with a Hewlett Packard vapor pressure osmometer to be 345 atm ± 10%, and the K value for cellulose acetate used in this experiment calculated from NaCl imbibition values was determined to be $1.9 \times 10^{-7} \, cm^2/hr \cdot atm$.

Figure 8:
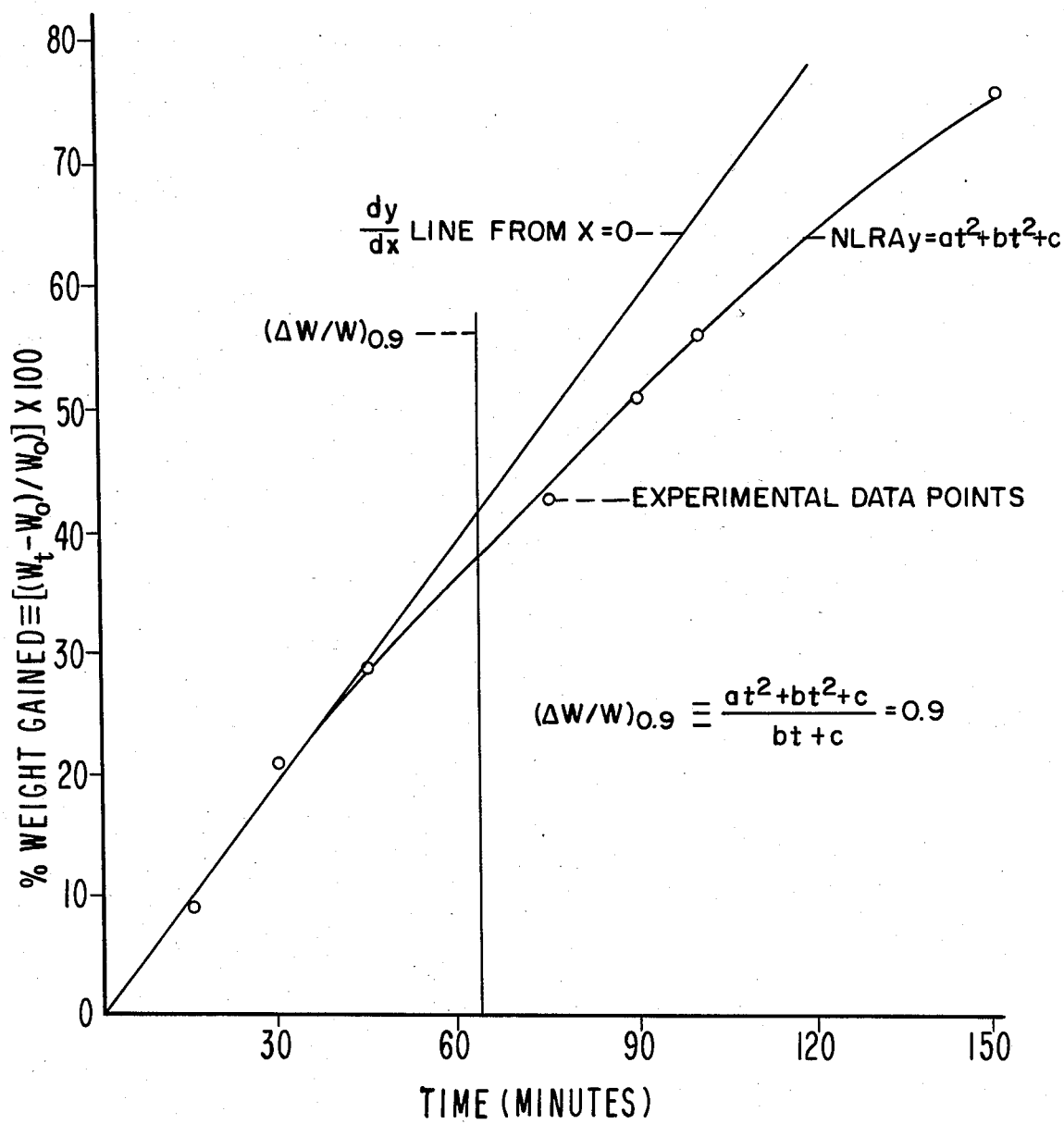
FIG. 8 represents the weight gain as a function of time for a polymer encapsulated in a semipermeable membrane when the encapsulated polymer is placed in water.

Substituting these values into the calculated $K\pi$ expression, $(1.9 \times 10^{-7}/cm^2/hr \, atm)(\pi) = 1.13 \times cm^2 hr$ gives $\pi = 600$ atm at $t=0$. As a method for evaluating the efficiency of a polymer with respect to duration of zero order driving force, the percent of water uptake was selected before the water flux values decreased to 90% of their initial values. The value of the slope for the equation of a straight line emanating from the percent weight gained axis will be equal to the initial value of dy/dt evaluated at t=0, with the y intercept c defining the linear swelling time, with (dy/dt) 0=0.665 and the y intercept=0, which yields y=0.665t+0.359. In order to determine when the value of the cumulative water uptake is 90% below the initial rate, the following expression is solved for t:

$$0.9 = \frac{at^2 + bt + c}{bt + c} = \frac{\Delta W}{w} 0.9 \quad (22)$$

$$\frac{0.00106\ t^2 + 0.665\ t + 0.359}{0.665t + 0.359} = 0.9 \quad (23)$$

and solving for t, $$-0.00106t^2 + 0.0065t + 0.0359 = 0 \quad (24)$$

$$t = \frac{-0.0665 + [(0.0665)^2 - 4(-0.00106)(0.0359)]^{\frac{1}{2}}}{2(-0.00106)}$$

t=62 min and the weight gain is $-0.00106(62)^2 + (0.665)(62) + 0.359 = 38$ μl, with the initial sample weight=100 mg, thus (Δw/w) 0.9×100=38%. The results are presented in FIG. 8 for a graphical representation of the values. Other methods available for studying the hydrogel solution interface include rheologic analysis, viscometric analysis, ellipsometry, contact angle measurements, electrokinetic determinations, infrared spectroscopy, optical microscopy, interface morphology and microscopic examination of an operative device.

The expression active agent as used herein, includes any beneficial agent, or beneficial compound, that can be delivered from the device to produce a beneficial and useful result. The agent can be insoluble to very soluble in the exterior fluid that enters the device and it can be mixed with an osmotically effective compound and as osmopolymer. The term active agent includes algicide, antioxidant, air purifier, biocide, bactericide, catalyst, chemical reactant, disinfectant, fungicide, fermentation agent, fertllity inhibitor, fertility promoter, germicide, plant growth promoter, plant growth inhibitor, preserative, rodenticide, sterilization agent, sex sterilant, and the like.

In the specification and the accompanying claims, the term beneficial agent also includes drug. The term "drug" includes any physiologically or pharmacologically active substance that produces a local or systemic effect, in animals, including warm blooded mammals, humans and primates; avians; household, sport and farm animals; laboratory animals; fishes; reptiles and zoo animals. The term "physiologically", as used herein, denotes the administration of a drug to produce generally normal levels and functions. The term "pharmacologically" denotes generally variations in response to the amount of drug administered to the host. See *Stedman's Medical Dictionary*, 1966, published by Williams and Wilkins, Baltimore, MD. The phrase drug formulation as used herein means the drug is in the compartment mixed with an osmotic solute and/or an osmopolymer and, if applicable, and with a binder and lubricant. The active drug that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autacoid systems, alimentary and excretory systems, inhibitory of autocoid systems, alimentary and excretory systems, inhibitory of autocoids and histamine systems. The active drug that can be delivered for acting on these recipients include anticonvulsants, analgesics, antiparkinsons, anti-inflammatories, calcium antagonists, anesthetics, antimicrobials, antimalarials, antiparasites, antihypertensives, antihistamines, antipyretics, alpha-adrenergic agnoist, alpha-blockers, biocides, bactericides, bronchial dilators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins, nonsteroidal anti-inflammatory drugs, angiotensin converting enzymes, polypeptide drugs, and the like.

Exemplary drugs that are very soluble in water and can be delivered by the osmotic devices of this invention include prochlorperazine edisylate, ferrous sulfate, aminocaproic acid, potassium chloride, mecaxylamine hydrochloride, procainamide hydrochloride, amphetamine sulfate, benzphetamine hydrochloride, isoproteronol sulfate, methamphetamine hydrochloride, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, cimetidine hydrochloride, theophylline cholinate, cephalexin hydrochloride, and the like.

Exemplary drugs that are poorly soluble in water and that can be delivered by the devices of this invention include diphenidol, meclizine hydrochloride, prochlorperazine maleate, phenoxybenzamine, thiethylperazine maleate, anisindone, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, esterogenic, progestational, corticosteroids, hydrocortisone, hydrocorticosterone acetate, cortisone acetate, triamcinolone, methyltesterone, 17 beta-estradiol, ethinyl estradiol, ethinyl estradiol 3-methyl ether, pednisolone, 17 beta-hydroxyprogesterone acetate, 19-nor-progesterone, norgestrel, norethindrone, norethisterone, norethiederone, progesterone, norgesterone, norethynodrel, and the like.

Examples of other drugs that can be delivered by the osmotic device include aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chloropromazine, methyldopa, dihydroxyphenylalanine, pivaloyloxyethyl ester of alpha-methyldopa hydrochloride, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captopril, madol, quanbenz, hydrochlorothiazide, ranitidine, flurbiprofen, fenbufen, fluprofen, tolmetin, alolofenac, mefenamic, flufenamic, difuninal, nimodipine, nitrendipine, nisoldipine, nicardipine, felodipine, lidoflazine, tiapamil, gallopamil, amlodipine, mioflazine, lisinolpril, enalapril, captopril, ramipril, endlapriat, famotidine, nizatidine, sucralfate, etintidine, tertatolol, minoxidil, chlordiazepoxide, chlordiazepoxide hydrochloride, diazepan, amitriptylin hydrochloride, impramine hydrochloride, imipramine pamoate, and the like. The beneficial drugs are known to the art in *Pharmaceutical Sciences*, 14th Ed., edited by Remington, (1979) published by Mack Publishing Co., Easton, PA; *The Drug, The Nurse, The Patient, Including Current Drug Handbook*, by Falconer, et al., (1974-1976) published by Saunder Company, Philadelphia, PA; *Medicinal Chemistry*, 3rd Ed., Vol. 1 and 2, by Burger, published by Wiley-Interscience, New York; and in *Physicians' Desk Reference*, 38 Ed., (1984) published by Medical Economics Co., Oradell, NJ.

The drug can be in various forms, such as uncharged molecules, molecular complexes, pharmacologically acceptable salts such as hydrochloride, hydrobromide, sulfate, laurate, palmitate, phosphate, nitrite, borate, acetate, maleate, tartrate, oleate and salicylate. For acidic drugs, salts of metals, amines or organic cations; for example, quarternary ammonium can be used. Derivatives of drugs such as ester, ethers and amides can be used. Also, a drug that is water insoluble can be used in a form that is water soluble derivative thereof to serve as a solute, and on its release from the device, is converted by enzymes, hydrolyzed by body pH or other metabolic processes to the original biologically active form. The agent, including drug, can be present in the compartment with a binder, dispersant, wetting agent, suspending agent, lubricant and dye. Representative of these include suspending agents such as acacia, agar, calcium carrageenan, alginic acid, algin, agarose powder, collagen, colloidal magnesium silicate, pectin, gelatin and the like; binders like polyvinyl pyrrolidone, lubricants such as magnesium stearate; wetting agents such as fatty amines, fatty quaternary ammonium salts, and the like. The phrase "drug formulation" indicates the drug is present in the compartment accompanied by an osmagent, osmopolymer, a binder, and/or the like. The amount of beneficial agent in a device generally is about from 0.05 ng to 5 g or more, with individual devices containing, for example, 25 ng, 1 mg, 5 mg, 10 mg, 25 mg, 125 mg, 250 mg, 500 mg, 750 mg, 1.0 g, 1.2 g, 1.5 g, and the like. The devices can be administered one, twice or thrice daily.

The solubility of a beneficial agent in the fluid can be determined by known techniques. One method consists of preparing a saturated solution comprising the fluid plus the agent as ascertained by analyzing the amount of agent present in a definite quantity of the fluid. A sample apparatus for this purpose consists of a test tube of medium size fastened upright in a water bath maintained at constant temperature and pressure, in which the fluid and agent are placed and stirred by a rotating glass spiral. After a given period of stirring, a weight of the fluid is analyzed and the stirring continued and additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may be not needed; if the agent has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in the *United States Public Health Service Bulletin*, No. 67 of the Hygienic Laboratory; *Encyclopedia of Science and Technology*, Vol. 12, pp 542 to 556, (1971) published by McGraw-Hill, Inc.; and *Encyclopedia Dictionary of Physics*, Vol. 6, pp 547 to 557, (1962) published in Pergamon Press, Inc.

The osmotic device of the invention is manufactured by standard techniques. For example, in one embodiment the beneficial agent is mixed with an osmagent and osmopolymer, and pressed into a solid possessing dimensions that correspond to the internal dimensions of the compartment adjacent to the passageway; or the beneficial agent and other formulation forming ingredients and a solvent are mixed into a solid or a semisolid by conventional methods such as ballmilling, calendering, stirring or rollmilling, and then pressed into a preselected shape. Next, a layer of a composition comprising an osmagent and an osmopolymer is laced in contact with the layer of beneficial agent formulation, and the two layers surrounded with a semipermeable wall. The layering of the beneficial agent composition and the osmagent/osmopolymer can be accomplished by conventional two-layer tablet press techniques. The wall can be applied by molding, spraying, or dipping the pressed shapes into wall-forming materials. Another and presently preferred technique that can be used for applying the wall is the air suspension coating procedure. This procedure consists in suspending and tumbling the pressed compositions in a current of air and a wall forming composition until the wall surrounds and coats the two pressed compositions. They form a laminated wall. The air suspension procedure is described in U.S. Pat. No. 2,799,241; *J. Am. Pharm. Assoc.* Vol. 48, pp 451 to 459 (1979); and, ibid. Vol. 49, pp 82 to 84 (1960). Other standard manufacturing procedures are described in *Modern Plastics Encyclopedia*, Vol. 46, pp 62 to 70 (1969); and in *Pharmaceutical Science*, by Remington, 14th Ed., pp 1626 to 1978 (1970), published by Mack Publishing Co., Easton, PA.

Exemplary solvents suitable for manufacturing the wall, the laminates and laminae, include inert inorganic and organic solvents, that do not adversely harm the materials and the final wall or the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DESCRIPTION OF EXAMPLES

The following examples are merely illustrative of the present invention, and they should not be considered as limiting the scope of the invention in any way, as these examples and other equivalents thereof will become apparent to those versed in the art in the light of the present disclosure, the drawings and the accompanying claims.

EXAMPLE 1

An osmotic delivery device manufactured in the appearance of an osmotic tablet shaped, sized and adapted for oral admittance into the gastrointestinal tract is made as follows: a first osmotic drug composition is prepared by screening 355 g of poly(ethylene oxide) having an approximate molecular weight of 200,000, through a 40 mesh stainless steel screen, then 100 g of a calcium antagonist is passed through the 40 mesh screen, 25 g of hydroxypropylmethylcellulose is passed through the 40 mesh screen and, finally, 10 g of potassium chloride is passed through the 40 mesh screen. Next, all the screened ingredients are added to the bowl of a laboratory blender and the ingredients dry blended for 15 to 20 minutes to produce a homogeneous blend. Then, a granulation fluid is prepared comprising 250 ml of ethanol and 250 ml of isopropyl alcohol, and the granulating fluid added to the blending bowl; first, 50 ml is sprayed into the bowl with constant blending, then 350 ml of the granulation fluid is added slowly to the bowl and the wet mass blended for another 15 to 20 minutes. Then, the wet granules are passed through a 16 mesh screen and dried at room temperature for 24 hours. Next, 10 g of magnesium stearate is added to the dry granules, and the ingredients roll-mixed for 20 to 30 minutes on a standard two-roll mill.

Next, a second osmotic composition is prepared as follows: first, 170 g of poly(ethylene oxide) having a molecular weight of 5,000,000 is screened through a 40 mesh screen, then 72.5 g of sodium chloride is passed through the 40 mesh screen, and the ingredients added to a mixing bowl and blended for 10 to 15 minutes. Then, a granulation fluid is prepared by mixing 350 ml of methanol and 150 ml of isopropyl alcohol, and the granulation fluid added to the blending bowl in two steps. First, 50 ml of the granulation fluid is sprayed into the bowl with constant blending; then 350 ml of the granulation fluid is slowly added to the bowl and the wet blend mixed for 15 to 20 minutes to a homogeneous blend. Then, the wet blend is passed through a 16 mesh screen, spread on a stainless steel tray and dried at room temperature of 22.5° C. for 24 hours. The dried blend is passed through a 16 mesh screen, then roll milled with 5 g of magnesium stearate on a two-roll mill for 20 to 30 minutes.

A number of drug cores are prepared by pressing the two compositions on a Manesty layerpress. The drug containing composition is fed into the cavity mold of the press and compressed into a solid layer. Then, the second osmotic composition is fed into the cavity overlaying the compressed layer and pressed into a solid layer to form a two-layered drug core.

Figure 9:
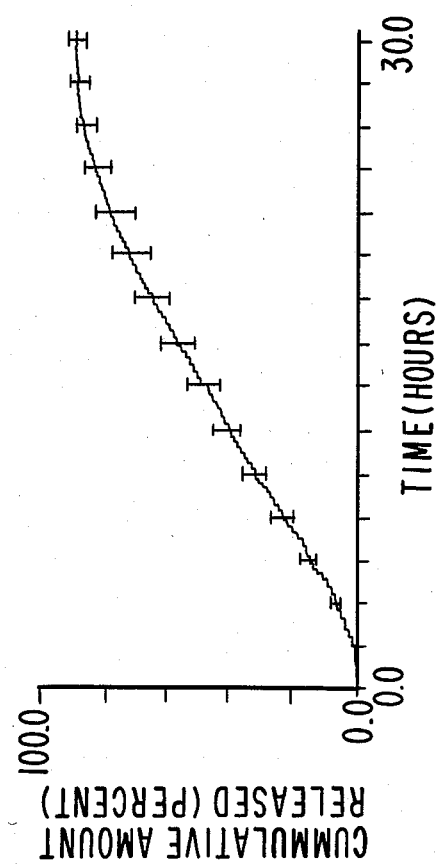
FIG. 9 depicts the cumulative amount of drug released from a device comprising two osmopolymer having two different molecular weights.

The drug cores next are coated with a semipermeable wall forming composition comprising 95 g of cellulose acetate having an acetyl content of 39.8% and 5 g of poly(ethylene glycol) 4000 in a solvent comprising 1960 ml of methylene chloride and 820 ml of methanol. The drug cores are coated with the semipermeable wall forming composition until the wall surrounds the drug core. A Wurster air suspension coater is used to form the semipermeable wall. The coated cores are then spread on a tray and the solvent evaporated in a circulating air oven for 50° C. for 65 hours. After cooling to room temperature, a 0.26 mm diameter passageway is laser drilled through the semipermeable wall connecting the exterior of the osmotic device with the composition continuing the drug. The osmotic device weighed 262 mg and it contained 30 mg of drug in the first composition weighing 150 mg, the second composition weighed 75 mg and the semipermeable wall weighed 37 mg. The first osmotic composition of the osmotic device comprises 30 mg of the calcium antagonists, 106 mg of poly(ethylene oxide), 3 mg of potassium chloride, 7.5 mg of hydroxypropylmethylcellulose and 3 mg of magnesium stearate. The second osmotic composition comprises 51 mg of poly(ethylene oxide), 22 mg of sodium chloride and 1.5 mg of magnesium stearate. The device has a diameter of 8 mm, a surface area of 1.8 cm$^2$ and the semipermeable wall is 0.17 mm thick. The cumulative amount of drug released is depicted in FIG. 9.

EXAMPLE 2

Osmotic delivery systems are prepared having a first composition comprising 25 to 1000 mg of a calcium channel blocker 100 to 325 mg of poly(ethylene oxide) having a molecular weight of 200,000, 2 to 10 mg of potassium chloride, 5 to 30 mg of hydroxypropylmethylcellulose, and 2 to 10 mg of magnesium stearate; and a second composition comprising 30 to 275 mg of poly(ethylene oxide) having a molecular weight of 5,000,000, 20 to 75 mg of sodium chloride and 1 to 5 mg of magnesium stearate. The procedure of Example 1 is repeated for preparing osmotic devices having the following compositions: (a) an osmotic device having a first composition comprising 60 mg of the calcium channel blocker 212 mg of poly(ethylene oxide), 6 mg of potassium chloride, 15 mg of hydroxypropylmethylcellulose and 6 mg of magnesium stearate; and a second composition comprising 102 mg of poly(ethylene oxide), 44 mg of sodium chloride, and 3 mg of magnesium stearate; and, (b) an osmotic device having a first composition comprising 90 mg of the calcium channel blocker, 318 mg of poly(ethylene oxide), 9 mg of potassium chloride, 22.5 mg of hydroxypropylmethylcellulose, and 146 mg of poly(ethylene oxide), 66 mg of sodium chloride, and 4.5 mg of magnesium stearate. In an embodiment, the osmotic device described in (a) and (b) further comprise a pulse coated layer of drug carried on the outer semipermeable wall. The pulse coat comprises 30 mg of the calcium channel blocker and hydroxypropylmethylcellulose. In operation in the fluid environment of use, the pulse coat provides instant drug availability for instant drug therapy.

EXAMPLE 3

An osmotic delivery system is prepared according to the procedure described above for administering a therapeutically effective amount of a member selected from the group consisting of nimodipine, nitrendipine, nisoldipine, nicardipine, felodipine, diltiazem, lidoflazine, tiapamil, gallopamil, amlodipine, and mioflazine.

EXAMPLE 4

An oral osmotic delivery device useful for the management of cardiovascular diseases is prepared according to the mode and manner of the invention. The device comprises a first composition, a drug composition, comprising 33 mg of a calcium antagonists, 122 mg of poly(ethylene oxide) having a molecular weight of 100,000, 8.25 mg of hydroxypropylmethylcellulose and 1.65 mg of magnesium stearate; and a second composition, a push composition, comprising 52.8 mg of poly(ethylene oxide) having a molecular weight of 5,000,000, 23.9 mg of sodium chloride, 4.13 mg of hydroxypropylmethylcellulose and 0.83 mg of magnesium stearate. The first and second composition are surrounded by a semipermeable wall comprising 95% cellulose acetate having an acetyl content of 39.8% and 5% poly(ethylene glycol) 4000. The osmotic device has at least one osmotic passageway 0.35 mm in diameter in the semipermeable wall connecting the drug composition with the exterior of the osmotic device. The device delivers 1.7 mg/hr of the drug over a prolonged period of 24 hours.

EXAMPLE 5

The procedure of Examples 1 to 3 is repeated for preparing osmotic devices containing from 5 mg to 150 mg of the drug. A series of osmotic devices are prepared containing 5 mg, 10 mg, 30 mg, 60 mg and 90 mg, up to 150 mg. These devices can comprise in the first composition from 50 mg to 750 mg of an osmopolymer and, optionally, 1 mg to 15 mg of an osmagent, and in the second composition from 20 mg to 320 mg of osmopolymer and 10 mg to 80 mg of osmagent. The devices have at least one osmotic passageway of 5 to 30 mils in diameter for delivering the drug. Individual devices can be prepared by following the procedures that have a rate of release of 0.25 mg, 0.5 mg, 0.6 mg, 0.8 mg, 1.3 mg, 2.7 mg and 3.0 mg per hour for 24 hours. The osmotic device is indicated for the management of plasma levels and it is indicated for treating cardiovascular conditions.

EXAMPLE 6

The procedures of the above examples are followed with all conditions as previously described except that the drug in the drug composition is an orally administered drug indicated for the management of cardiovascular diseases and it is a member selected from the group consisting of fendiline, diltiazem, perhexiline, and prenylamine.

EXAMPLE 7

An osmotic therapeutic device for the controlled and the continuous oral release of the beneficial calcium channel blocker drug verapamil is made as follows: 90 mg of verapamil, 50 mg of sodium carboxylvinyl polymer having a molecular weight of 200,000 and sold under the trademark Carbopol ® polymer, 3 mg of sodium chloride, 7.5 mg of hydroxypropylmethylcellulose and 3 mg of magnesium stearate are mixed thoroughly as described in Example 1, and pressed in a Manesty press with a 5/16 inch punch using a light pressure to produce a layer of the drug composition. Next, 51 mg of the carboxyvinyl polymer having a molecular weight of 3,000,000 and sold under the trademark Carbopol ® polymer, 22 mg of sodium chloride and 2 mg of magnesium stearate are blended thoroughly and added to the Manesty press, and pressed to form a layer of expandable, osmotic composition in contact with the layer of osmotic drug composition.

Next, a semipermeable wall is formed by blending 170 g of cellulose acetate having an acetyl content of 39.8% with 900 ml of methylene chloride and 400 ml of methanol, and spray coating the two layered compartment forming member in an air suspension machine until 5.1 mil thick semipermeable wall surrounds the compartment. The coated device is dried for 72 hours at 50° C. and then a 8 mil osmotic passageway is laser drilled through the semipermeable wall to connect the layer containing drug with the exterior of the device for releasing drug over a prolonged period of time.

EXAMPLE 8

An osmotic therapeutic drug delivery device is prepared by following the procedure of Example 5, with all manufacturing conditions as described heretofore, except that in the present example the drug composition comprises 90 mg of verapamil, 50 mg of sodium carboxyvinyl polymer having a molecular weight of 200,000, 7.5 mg of hydroxypropylmethylcellulose and 3 mg of magnesium stearate.

EXAMPLE 9

An osmotic, therapeutic device for the delivery of the drug ketoprofen for uses as an anti-inflammatory is prepared by first pressing in a Manesty press an osmotic drug composition containing 75 mg of ketoprofen, 300 mg of sorbitol, 30 mg of sodium bicarbonate, 26 mg of pectin, 10 mg of polyvinyl pyrrolidone, and 5 mg of stearic acid, and pressing the composition in a cavity to a solid layer. Next, the cavity is charged with a second and greater force generating composition comprising 122 mg of pectin having a molecular weight of 90,000 to 130,000, 32 mg of mannitol, 20 mg of polyvinyl pyrrolidone, and 2 mg of magnesium stearate and pressed to form a second layer in contacting relation with the first layer. The second layer had a density of 1.28 g/cm$^3$ and a hardness score of greater than 12 kP. Next, the two layer core is surrounded with a semipermeable wall comprising 85 g of cellulose acetate having an acetyl content of 39.8%, and 15 g of polyethylene glycol 4000, 3(wt/wt)percent solid in a wall forming solvent comprising 1960 ml of methylene chloride and 819 ml of methanol. The coated device is dried for 72 hours at 50° C., and then a 0.26 mm diameter passageway is laser drilled through the wall. The semipermeable wall is 0.1 mm thick, the device has an area of 3.3 cm$^2$, and it releases drug over a 12 hour period.

EXAMPLE 10

The procedure of Example 9 is followed for providing an osmotic device wherein the compartment contained a blend of osmopolymers. The compartment contained a first composition weighing 312 mg and consists of 48% ketoprofen drug, 38% poly(ethylene oxide) osmopolymer having a molecular weight of 200,000, 10% poly (ethylene glycol) osmopolymer having a molecular weight of 20,000, 2% sodium chloride and 2% magnesium stearate; and a second composition weighing 150 mg and consisting of 93% poly(ethylene oxide) having a molecular weight of 5,000,000, 5% sodium chloride and 2% magnesium stearate.

EXAMPLE 11

Figure 10:
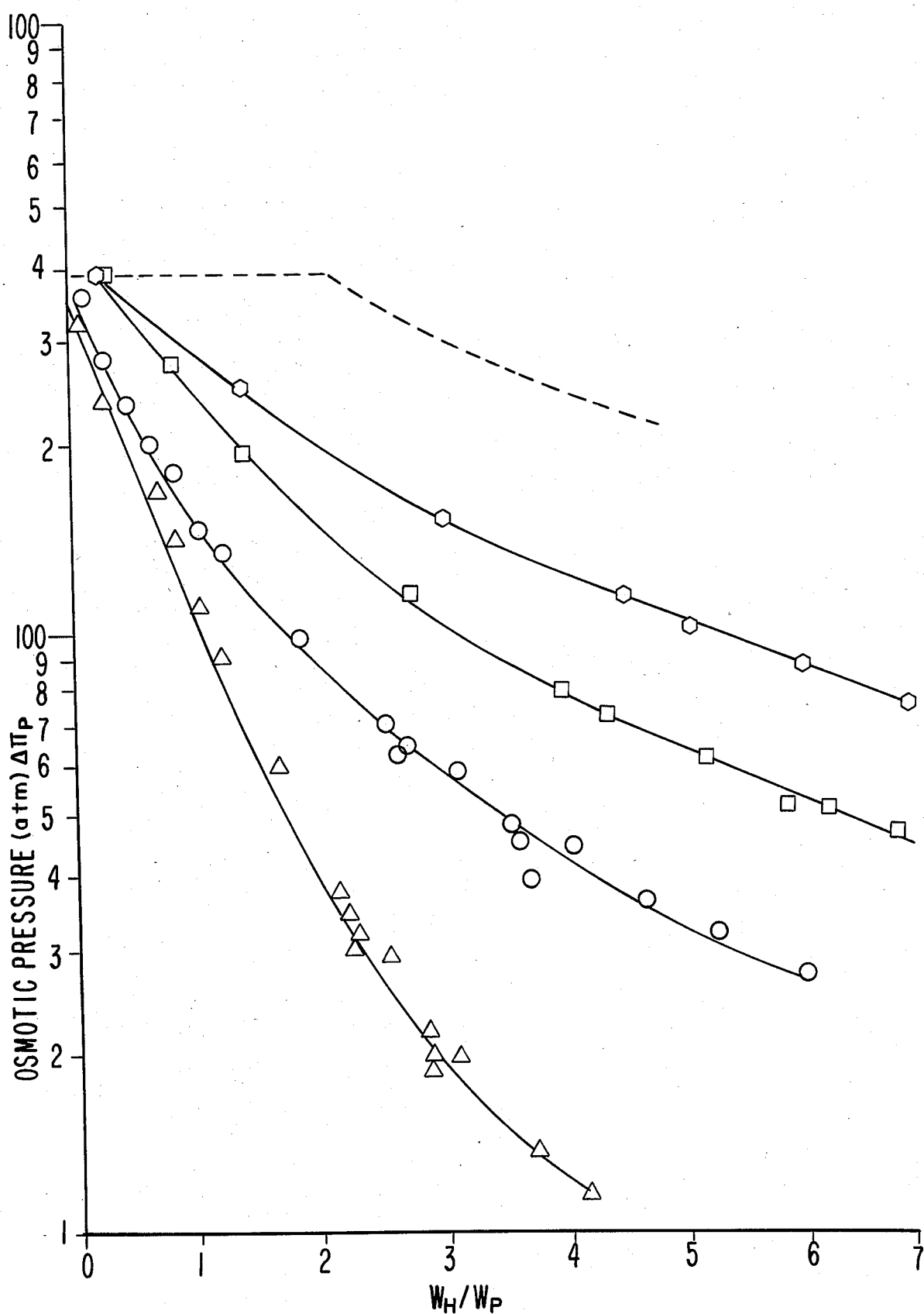
FIG. 10 depicts the osmotic pressure curves for an osmagent and a number of osmopolymer/osmagent compositions; and, FIG. 11 illustrates the in vivo and in vitro cumulative release for a drug delivered by an osmotic device.

In this example, the increase in osmotic pressure for a number of compositions comprising an osmagent and an osmopolymer are measured for demonstrating the operative advantage provided by the invention. The measurements are made by measuring the amount of water imbibed across the semipermeable wall of a bag containing an osmagent, or an osmopolymer, or a composition comprising an osmagent and an osmopolymer. The semipermeable wall of the bag is formed of cellulose acetate having an acetyl content of 39.8%. The measurements are made by weighing the dry ingredients of the semipermeable bag, followed by weighing the blotted semipermeable bag, after the bag is in a water bath at 37° C. for various lengths of time. The increase in weight is due to water imbibition across the semipermeable wall caused by the osmotic pressure gradient across the wall. The osmotic pressure curves are illustrated in FIG. 10. In FIG. 10 the curved line with the triangles represents the osmotic pressure for poly(ethylene oxide) having a molecular weight of 5,000,000; the curved line with the circles represents the osmotic pressure for a composition comprising poly(ethylene oxide) having a molecular weight of 5,000,000 and sodium chloride with the ingredients present in the composition in the ratio of 9.5 parts osmopolymer to 0.5 parts osmagent; the curved line with squares represents a composition comprising the same osmopolymer and osmagent in the ratio of 9 parts osmopolymer to one part osmagent; the curved lines with hexagon represents the same composition comprising the osmopolymer an osmagent in the ratio of 8 parts to 2 parts; and, the dashed lines represent the osmagent sodium chloride. The mathematical calculations are made using the formula $dw/dt = K\Delta\pi A/h$, wherein $dw/dt$ is the rate of water imbibition over time, A is the area of the semipermeable wall, and K is the permeability coefficient. Also, in FIG. 10, $W_H/H_p$ is the amount of water imbibed divided by the dry weight of osmopolymer plus osmagent.

EXAMPLE 12

An osmotic therapeutic device for dispensing naproxen is prepared by screening through a 40 mesh screen a composition comprising 49% of naproxen, 46% poly(ethylene oxide) having a molecular weight of 100,000, and 3% hydroxyproylmethylcellulose, and then blending the screened composition with an alcohol solvent used in the ratio of 75 ml of solvent to 100 g of granulation. The wet granulation is screened through a 16 mesh screen, dried at room temperature for 48 hours under vacuum, and blended with 2% magnesium stearate that has been passed through an 80 mesh screen. The composition is compressed as described above.

Next, a composition comprising 73.9% of pectin having a molecular weight of 90,000 to 130,000, 5.8% microcrystalline cellulose, 5.8% polyvinyl pyrrolidone, 14.3% sodium chloride and 2% sucrose is passed through a 40 mesh screen, blended with an organic solvent in the ratio of 100 ml of solvent to 100 g of granulation for 25 minutes, passed through a 16 mesh screen, dried for 48 hours at room temperature under vacuum, again passed through a 16 mesh screen, blended with 2% magnesium stearate and then compressed onto the compressed layer described in the above paragraph. The dual layered drug core is coated by dipping in a wall forming composition comprising 80% cellulose acetate having an acetyl content of 39.8%, 10% polyethylene glycol 4000, and 10% hydroxypropylmethylcellulose. An osmotic passageway is drilled through the wall communicating with the drug containing composition. The osmotic diameter is 0.38 mm.

EXAMPLE 13

The procedure of Example 10 is repeated with all conditions as described, except that the osmopolymer in the drug composition is polyoxyethylene-polyoxypropylene block copolymer having a molecular weight of about 12,500.

EXAMPLE 14

Figure 11:
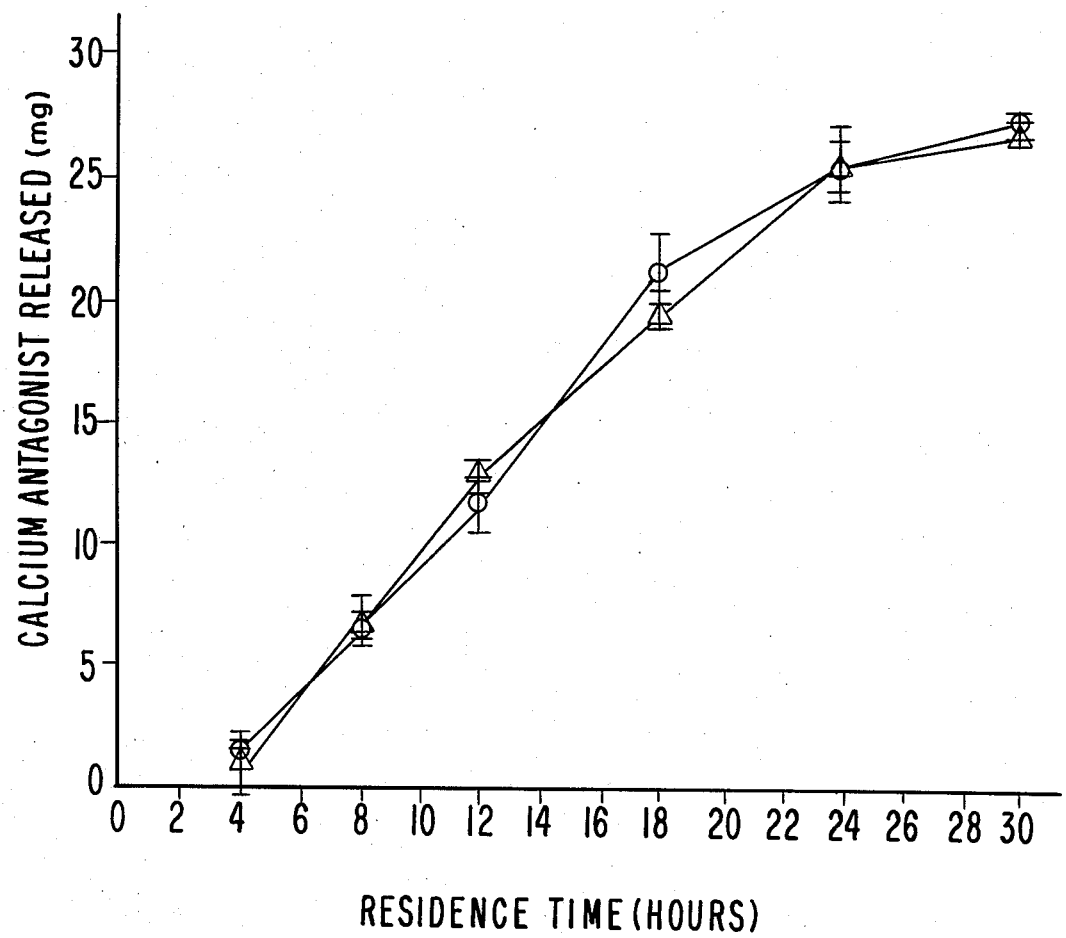

The in vivo and in vitro mean cumulative release of a calcium antagonist from an osmotic device comprising a composition adjacent to the passageway comprising 30 mg of the drug, 106.5 mg of poly(ethylene oxide) having a molecular weight of 200,000, 3 mg of potassium chloride, 7.5 mg of hydroxypropylmethylcellulose, and 3 mg of magnesium stearate; a composition distant from the passageway comprising 52 mg of poly(ethylene oxide) having a molecular weight of 5,000,000, 22 mg of sodium chloride and 1.5 mg of magnesium stearate; and a semipermeable wall comprising 95% cellulose acetate having an acetyl content of 39.8% and 5% hydroxypropylmethylcellulose is measured in vivo in laboratory dogs and in vitro in the laboratory. The amounts of drug released at various times in vivo were determined by administering a series of devices to the animals and measuring the amount released from the corresponding device at the appropriate residence time. The results are depicted in FIG. 11. In FIG. 11 the circles represent the in vivo cumulative release and the triangles represent the in vitro mean cumulative release.

EXAMPLE 15

The procedure of Example 11 is followed for making an osmotic therapeutic delivery system comprising: a first drug composition weighing 638 mg and consisting of 96% cephalexin hydrochloride, 2% Povidone (polyvinyl pyrrolidone) and 2% magnesium stearate; a second, or osmotic driving composition weighing 200 mg and consisting of 68.5% poly(ethylene oxide) having a molecular weight of 5,000,000, 29.5% sodium chloride, and 2% magnesium stearate; a semipermeable wall weighing 55.8 mg consisting of 80% cellulose acetate having an acetyl content of 39.8%, 10% polyethylene glycol 4000, and 10% hydroxypropylmethylcellulose; and an osmotic orifice having a diameter of 0.39 mm. The device has an average rate of release of about 54 mg per hour over a period of 9 hours.

EXAMPLE 16

The procedures described above are followed in this example for manufacturing an osmotic device for delivering the antipsychotic drug haloperidol to the gastrointestinal tract of a human. The osmotic delivery system comprises a first or drug composition comprising 11 mg of haloperidol, 245 mg of poly(ethylene oxide) having a molecular weight of about 100,000, 13.8 mg of hydroxypropylmethylcellulose and 5.5 mg of magnesium stearate; and, a second composition, initially in laminar arrangement with the first composition, which second composition consists essentially of 122 mg of poly(ethylene oxide) having a molecular weight of about 5,000,000, 56 mg of sodium chloride, 10 mg of hydroxypropylmethylcellulose and 0.95 mg of magnesium stearate. The two compositions are surrounded by a semipermeable wall comprising 22.5 mg of cellulose acetate having an acetyl content of 39.8% and 2.5 mg of poly(ethylene glycol) 3350. The device has an osmotic passageway of 0.36 mm. The device delivers about 0.8 mg per hour over a 14 hours time period.

EXAMPLE 17

The procedures of Examples 16 is repeated for preparing a series of osmotic devices housing a drug composition containing from 1 mg to 125 mg of haloperidol for dispensing a dosage of 0.1 mg, 1 mg, 2 mg, or 10 mg per hour over a prolonged period of at least 12 hours, or a cumulative dosage of 0.01 mg/kg/day to 0.075 mg/kg/day. The osmotic devices can be administered once, twice or thrice a day.

EXAMPLE 18

The procedure set forth above is repeated for providing an osmotic device for dispensing the nonsteroidal, anti-inflammatory, antipyretic, analgesic drug ibuprofen. The oral osmotic device comprises a first lamina composition consisting of 198 mg of ibuprofen and a second lamina composition consisting of 132 mg of poly(ethylene oxide) having a molecular weight of 5,000,000. The laminae compositions are surrounded by a semipermeable wall consisting essentially of 100%, 48.1 mg of cellulose acetate having an acetyl content 32%. The device has an osmotic passageway connecting the first lamina composition with the exterior of the device. The device has an average rate of release of 12.7 mg per hour over a 12 hour dispensing period. Similar osmotic devices are prepared containing 50 mg, 150 mg, 200 mg, 300 mg, 400 mg, 500 mg, and 600 mg for the anti-inflammatory, analgesic and antipyretic activities.

EXAMPLE 19

The procedures described above are followed for providing an osmotic device housing the non-steroidal drug with anti-inflammatory, antipyretic and analgesic properties, indomethacin. The compartment of the device houses a first layer comprising 50 mg of indomethacin, 8.3 mg of hydroxypropylmethylcellulose, 3.3 mg of magnesium stearate and 105 mg of poly(ethylene oxide) having a molecular weight of 100,000; and a second layer consisting of 52.5 mg of poly(ethylene oxide) having a molecular weight of 5,000,000, 24.2 mg of sodium chloride, 4.2 mg of hydroxypropylmethylcellulose and 1.67 mg of magnesium stearate. The device has a semipermeable wall comprising 95% (19.0 mg) of cellulose acetate having an acetyl content of 39.8%, and 5% (1 mg) of poly(ethylene glycol) 4000. The device has an osmotic passageway of 0.36 mm diameter for release of indomethacin. The device delivers 93% of the indomethacin over 18 hours. Similar devices are provided housing 25 mg and 75 mg of indomethacin for administering b.i.d. or t.i.d. for establishing steady-state plasma levels.

EXAMPLE 20

The procedures described above are followed for providing an osmotic device comprising a drug layer of 80 mg of isosorbide dinitrate, 80 mg of lactose, 208 mg of poly(ethylene oxide) having a molecular weight of 200,000, 19.5 mg of hydroxypropylmethylcelullose and 3.9 mg of magnesium stearate, and a second expandable layer of 239 mg of poly(ethylene oxide) having a molecular weight of 5,000,000, 13 mg of hydroxypropylmethylcellulose, and 5.2 mg of magnesium stearate. The device has a semipermeable wall comprising 80% (36 mg) of cellulose acetate having an acetyl content of 39.8%, 10% (4.5 mg) of poly(ethylene glycol) 4000, and 10% (4.5 mg) of hydroxypropylmethylcellulose. The device has an osmotic passageway with a diameter of 0.51 mm and is clinically indicated for the relaxation of smooth muscle and treating angina pectoris.

EXAMPLE 21

The procedures described above are followed for making an osmotic device comprising a drug layer of 250 mg of alpha-methyldopa, levo-3-(3,4-dihydroxyphenyl)-2-methylalamine, 97.2 mg of poly(ethylene oxide) having a molecular weight of 200,000, 18.5 mg of hydroxypropylmethylcellulose and 8.7 mg of magnesium stearate, and a second layer of 226.6 mg of poly(ethylene oxide) having a molecular weight of 5,000,000, 12.3 mg of hydroxypropylmethylcellulose, and 4.9 mg of magnesium stearate. The device has a semipermeable wall comprising 65 wt. percent, (15.5 mg), of cellulose acetate having an acetyl content of 39.8%, 17.5 wt. percent (4.2 mg), poly(ethylene glycol) 3350, and 17.5 wt. percent (4.2 mg) of hydroxypropylmethylcellulose. The device has an osmotic passageway of 0.51 mm communicating with the drug lamina for dispensing the drug from the device. The drug is indicated as an antihypertensive possessing decarboxylose inhibitor action in animals and in man. Similar devices can be prepared housing 125 mg to 500 mg of the drug.

EXAMPLE 22

The procedures described above are followed for providing an osmotic device comprising a first drug layer comprising 50 mg of hydrochlorothiazide, 189 mg of poly(ethylene oxide) having a molecular weight of 200,000, 1.0 mg of hydroxypropylmethylcellulose, and 2.5 mg of magnesium stearate; and a second expandable push layer comprising 280 mg of poly(ethylene oxide) having a molecular weight of 5,000,000, 15.4 mg of hydroxypropylmethylcellulose, and 0.2 mg of magnesium stearate. The device has a semipermeable wall comprising 95 wt. percent (54.4 mg) of cellulose acetate having an acetyl content of 39.8% and 5 wt. percent (2.9 mg) of poly(ethylene glycol) 3350. The device has an osmotic passageway with a diameter of 0.51 mm in the semipermeable wall communicating with the drug. Clinically, hydrochlorothiazide is a diuretic-antihypertensive. The osmotic device can contain from 12.5 to 250 mg given in 1 to 3 doses daily.

EXAMPLE 23

The procedures described above are followed for providing an osmotic device comprising a first drug layer comprising of 6 mg of an alpha adrenoreceptor blocker, 135 mg of poly(ethylene oxide) having a molecular weight of 100,000, 7.5 mg of hydroxypropylmethylcellulose, and 3.0 mg of magnesium stearate; and an expandable push layer initially in close contacting arrangement comprising 47.3 mg of poly(ethylene oxide) having a molecular weight of 5,000,000, 21.8 mg of sodium chloride, 3.8 mg of hydroxypropylmethylcellulose, and 1.5 mg of magnesium stearate. The device has a semipermeable wall comprising 5 wt. percent (25 mg) of cellulose acetate having an acetyl content of 39.8, and 5 wt. percent (1.32 mg) of poly(ethylene glycol) 4000. The device has an osmotic passageway of 0.37 mm. The device, after a start-up of about 1 hour, delivers about 0.24 mg per hour over a period of 26 hours. Devices containing from 1 mg to 125 mg of drug can by prepared for their vasodilator effect as related to blockade of postsynaptic alpha-adrenoceptors. The device also can be used for the treatment of hypertension.

EXAMPLE 24

The procedure of EXAMPLE 23 is repeated for providing osmotic devices containing in the first layer from 1 mg to 15 mg of a blocking alpha adrenoreceptor from 25 mg to 375 mg of osmopolymer and, optionally, from 0.5 mg to 7.5 mg of osmagents and a second layer comprising 15 mg to 250 mg of osmopolymer and, optionally, from 10 mg to 75 mg of osmagent.

EXAMPLE 25

The procedure of EXAMPLE 23 is followed for providing an osmotic device comprising: a first layer composition weighing 150.70 mg comprising 4 wt. percent of a blocking alpha-adrenoreceptor drug, 89 wt. percent Polyox®N-10 poly(ethylene oxide) having a molecular weight of 100,000, 5 wt. percent hydroxypropylmethylcellulose, and 2 wt. percent magnesium stearate; a second layer composition weighing 150.70 mg comprising 92 wt. percent Polyox® Coagulant poly(ethylene oxide) having a molecular weight of 5,000,000, 5 wt. percent hydroxypropylmethylcellulose, 1 wt. percent ferric oxide, and 2 wt. percent magnesium stearate. The osmotic device semipermeable wall weighed 23.70 mg comprising 95 wt. percent cellulose acetate having an acetyl content of 39.8% and 5 wt. percent poly(ethylene glycol) 4000. The osmotic passageway has a diameter of 0.370 mm connecting the exterior of the device with the drug layer.

EXAMPLES 26-27

The procedures described above are repeated with all procedures as previously described, except that the osmotic device contained an alpha-adrenergic blocking drug selected from the the group consisting of trimazosin, phenoxybenzamine hydrochloride and phentolamine hydro- chloride.

EXAMPLES 28-31

The procedures described above are repeated with all procedures as described, except that in the present devices the first composition in the compartment contained from 1 mg to 125 mg of a member selected from the group consisting essentially of anhydrous theophylline, salbutamol base, diazepam and furosemide.

EXAMPLES 32-36

The procedures for manufacturing an osmotic device for dispensing an angiotensin converting enzyme drug through at least one pore in a cellulose acylate wall of the device is manufactured as describe herein with the angiotensin converting enzyme inhibitor a member selected from the group consisting of lisinopril, enalapril, captopril, ramipril and enalapriat.

EXAMPLES 37-41

The procedures for manufacturing an osmotic device for administering a gastrointestinal histamine receptor antagonists in a therapeutically effective amount for treating ulcers through at least one pore-passageway of a cellulosic wall is followed with the manufacture as set forth with the drug selected from the group consisting of famotidine, cimetidine, ranitidine, nizatidine and etintidine, from 100 mg to 450 mg every 12 to 24 hours one to three times daily.

EXAMPLE 42

A dosage form for administering the beneficial, gastrointestinal administrable drug, salbutamol hydrochloride, is made according to the above procedures. The wall in the present example is applied in an air suspension machine and it comprises a microporous wall-forming composition. The microporous composition comprises 45% by weight of cellulose acetate having an acetyl content of 39.8%, 45% by weight of sorbitol, and 10% by weight of polyethylene glycol 400. In operation, in the fluid environment of the gastrointestinal tract, the sorbitol is leached from the wall providing thereby a plurality of microporous passageways of controlled porosity for release of the drug salbutamol hydrochloride from the dosage forms.

EXAMPLE 43

A dosage form for administering the beneficial gastrointestinal administrable drug, theophylline isopropanolamine is made according to the above procedures. The wall in the present example is applied in an air suspension machine and it comprises a microporous wall-forming composition. The microporous composition comprises 55% by weight of cellulose acetate having an acetyl content of 39.8%, 40% by weight of sorbitol and 5% by weight of polyethylene glycol 400. In operation, in the fluid environment of the gastrointestinal tract, the sorbitol is leached from the wall providing a plurality of micropores. The micropores of controlled porosity provide fluid access through the wall to the osmopolymers. The osmopolymers act in concert to deliver the drug through a preformed passageway in the wall to the drug formulation.

The novel osmotic system of this invention uses dual means for the attainment of precise release rate of drugs that are difficult to deliver in the environment of use, while simultaneously maintaining the integrity and the character of the system. While there has been described and pointed out features and advantages of the invention as applied to the presently preferred embodiments, those skilled in the dispensing art will appreciate that various modifications, changes, additions, and omissions in the system illustrated and described can be made without departing from the spirit of the invention.

We claim:

1. An osmotic device for the oral administration at a controlled rate a beneficial angiotensin converting enzyme inhibitor to an enviromment of use, the osmotic device comprising:
   (a) a wall comprising at least in part a composition permeable to the passage of an exterior fluid present in the environment of use, the wall surrounding and forming:
   (b) a compartment;
   (c) a first composition in the compartment, said first composition comprising a dosage amount of an angiotensin converting enzyme inhibitor and an osmopolymer that exhibits an osmotic pressure gradient across the wall aganist an external aqueous fluid, which osmopolymer imbibes and absorbs aqueous fluid that enters the compartment to form a dispensable composition comprising the angiotension converting enzyme inhibitor;
   (d) a second composition in the compartment, said second composition comprising an osmopolymer that exhibits an osmotic pressure gradient across the wall against an external fluid; and, (e) at least one passageway in the wall connecting the exterior of the device with the interior of the device for delivering the composition comprising the angiotensin converting enzyme inhibitor from the osmotic device.

2. The osmotic device for the oral administration at a controlled rate the beneficial angiotensin converting enzyme inhibitor according to claim 1, wherein the second composition comprises an osmotically effective solute that exhibits an osmotic pressure gradient, across the semipermeable wall against an external fluid.

3. A method for administering a beneficial angiotensin converting enzyme inhibitor drug to a warm blooded animal, which method comprises:
(a) admitting an osmotic device orally into the animal, said osmotic device comprising:
(1) a shaped semipermeable wall comprising a composition permeable to the passage of an exterior fluid and substantially impermeable to the passage of the beneficial drug, the wall surrounding and forming:
(2) a compartment containing a first composition comprising a dosage unit amount of the beneficial angiotensin converting enzyme inhibitor and an osmopolymer that exhibits an osmotic gradient across the semipermeable wall against an external fluid, which osmopolymer imbibes aqueous fluid into the compartment and forms a dispensable composition comprising the angiotensin converting enyzme inhibitor, and a second composition comprising an osmopolymer that exhibits an osmotic pressure gradient across the semipermeable wall against an external fluid;
(3) at least one passageway in the wall connecting the exterior of the osmotic device with the first composition; and
(b) administering the beneficial angiotensin converting enzyme inhibitor to the animal by imbibing fluid through the semipermeable wall into the osmotic device to form a dispensable first composition comprising the angiotensin converting enzyme inhibitor, and by the second composition expanding, whereby the angiotensin converting enzyme inhibitor is administered by the combined actions of the first and second compositions through a passageway to the animal over time.

4. An osmotic device for orally administering a calcium antagonist drug to an environment of use, the osmotic device comprising:
(a) a wall permeable at least in part to the passage of fluid, which wall surrounds and forms,
(b) a compartment housing a first composition comprising a beneficial calcium antagonist drug and an osmopolymer that exhibits an osmotic pressure gradient across the wall against a fluid and imbibes fluid into the compartment to form a composition comprising the calcium antagonist drug, and a second composition comprising an osmopolymer that exhibits an osmotic pressure gradient across the wall against a fluid; and
(c) a passageway in the wall communicating with the first composition and the exterior of the device for delivering the first composition comprising the beneficial calcium antagonist drug through the passageway to the environment of use from the device.

5. A method for managing the plasma levels in a patient on a calcium channel blocker drug, which method comprises administering orally a therapeuctically effective amount of a calcium channel blocker drug to a patient from an osmotic device, which device comprises: a semipermeable wall permeable at least in part to the passage of an exterior fluid and substantially impermeable to the passage of the calcium channel blocker drug, the wall surrounding and forming: a compartment comprising a first composition comprising a dosage amount of the calcium channel blocker drug and an osmopolymer that exhibits an osmotic pressure gradient across the wall against an exterior fluid, and a second composition comprising a different osmopolymer that exhibits an osmotic pressure gradient across the wall against an exterior fluid; at least one passageway in the wall communicating the exterior of the device with the first composition; and, delivering the composition comprising calcium channel blocker drug through a passageway to the patient for managing the plasma levels.

6. A dosage form for administering at a controlled rate a histamine receptor blocking drug to a warm blooded animal, which dosage form comprises:
(a) a wall comprising at least in part a composition permeable to the passage of an exterior fluid present in the environment of use an substantially impermeable to the passage of the histamine receptor blocking drug, the wall surrounding and forming:
(b) a compartment;
(c) a first composition in the compartment, said first composition comprising a beneficial histamine receptor blocking drug and an osmoplolymer that exhibits an osmotic pressure gradient across the wall against an external fluid and forms a dispensable composition with fluid that enters the compartment;
(d) a second composition in the compartment, said second composition comprising an osmopolymer that exhibits an osmotic pressure gradient across the wall against an external fluid; and,
(e) at least one passageway in the wall communicating with the compartment and the exterior of the dosage form for delivering the composition comprising the beneficial histamine receptor blocking drug through the passageway from the dosage form.

7. The dosage form for administering at a controlled rate the histamine receptor blocking drug according to claim 6, wherein the passageway is a pore passageway.

8. The dosage form for administering at a controlled rate the histamine receptor blocking drug according to claim 6, wherein the second composition comprises an osmotically effective compound that exhibits an osmotic pressure gradient across the wall against a fluid.

9. An osmotic device for delivering at a controlled rate a beneficial agent to an enviromnent of use, the osmotic device comprising:
(a) a wall comprising in at least a part a semipermeable composition permeable to the passage of an exterior fluid present in the environment of use and substantially impermeable to the passage of a beneficial agent, which wall surrounds and forms:
(b) a compartment comprising (1) a first means for delivering a beneficial agent, said first means comprising a beneficial agent and an osmopolymer that forms a dispensable first means with fluid that enters the compartment; and, (2) a second means for assisting the first means for delivering the beneficial agent, said second means comprising an osmopolymer; and, (c) a passageway in the wall communicating with the first means and the exterior of the device for delivering the first means comprising the beneficial agent from the device.

10. The osmotic device for delivering at a controlled rate the beneficial agent according to claim 9, wherein the semipermeable composition comprises a member selected from the group consisting of cellulose acylate, cellulose diacylate, cellulose triacylate, cellulose acetate, cellulose diacetate, cellulose triacetate, cellulose ester, cellulose ether and cellulose ester ether.

11. The osmotic device for the delivery at a controlled rate the beneficial agent according to claim 9, wherein the first means is in the compartment as a layer, and the second means is in the composition as a layer.

12. The osmotic device for the delivery at a controlled rate the beneficial agent according to claim 9 wherein the first means imbibes external fluid through the wall into the compartment, and the second means imbibes external fluid through the wall into the compartment.

13. The osmotic device for the delivery at a controlled rate the beneficial agent according to claim 9, wherein the osmopolymer comprising the second means has a molecular weight greater then the molecular weight of the osmopolymer comprising the first means.

14. The osmotic device for delivering at a controlled rate the beneficial agent according to claim 9, wherein the beneficial agent is theophylline.

15. The osmotic device for delivering at a controlled rate the beneficial agent according to claim 9, wherein the beneficial agent is salbutamol.

16. The osmotic device for delivering at a controlled rate the beneficial agent according to claim 9, wherein the beneficial agent is diazepam.

17. The osmotic device for delivering at a controlled rate the beneficial agent according to claim 9, wherein the beneficial agent is furosemide.

18. The osmotic device for delivering at a controlled rate the beneficial agent according to claim 9, wherein the beneficial agent is hydrochlorothiazide.

19. The osmotic device for delivering at a controlled rate the beneficial agent according to claim 9, wherein the beneficial agent is alpha-methyldopa.

20. The osmotic device for delivering at a controlled rate the beneficial agent according to claim 9, wherein the beneficial agent is isosorbide dinitrate.

21. The osmotic device for delivering at a controlled rate the beneficial agent according to claim 9, wherein the beneficial agent is indomethacin.

22. The osmotic device for delivering at a controlled rate the beneficial agent according to claim 9, wherein the beneficial agent is ibuprofen.

23. The osmotic device for delivering at a controlled rate the beneficial agent according to claim 9, wherein the beneficial agent is haloperidol.

24. The osmotic device for delivering at a controlled rate the beneficial agent according to claim 9, wherein the beneficial agent is a member selected from the group consisting of lisinopril, ramipril, enalapril, captopril and enalapriat.

25. The osmotic device for delivering at a controlled rate the beneficial agent according to claim 9, wherein the beneficial agent is a member selected from the group consisting of famatidine, cimetidine, ranitidine, nizatidine, sucralfate and etintidine.

26. The osmotic device for delivering at a controlled rate the beneficial agent according to claim 9, wherein the device comprises a plurality of passageways.

27. The osmotic device for delivering at a controlled rate the beneficial agent according to claim 9, wherein the passageway is a microporous member.

28. The osmotic device for delivering at a controlled rate the beneficial agent according to claim 9, wherein the passageway comprises at least one pore.

29. A device for the controlled delivery of a beneficial drug to a biological enviromnent of use, comprising:

(a) a shaped wall that permits an exterior fluid present in the environment of use to enter the device, the wall surrounding and forming:

(b) a compartment comprising (1) a composition comprising a dosage amount of a drug, and a polymer that exhibits a gradient across the wall against an external fluid and forms a dispensable composition with fluid that enters the device, and (2) a composition comprising an osmotically effective compound that exhibits a gradient across the wall against external fluid, and a polymer that exhibits a gradient across the wall against an external fluid; and, (c) a passageway in the wall communicating with the exterior of the device and the composition the drug for delivering a therapeutically effective amount of drug from the device at a controlled rate over a prolonged period of time.

30. The device for the controlled delivery of the beneficial drug to the biological environment of use according to claim 29, wherein the device when in operation in the environment of use, the polymer present in composition (1) comprising the drug imbibes fluid through the wall into the compartment for hydrodynamically delivering the drug from the osmotic device.

31. The device for the controlled delivery of the beneficial drug ot the biological environment of use according to claim 29, wherein the device comprises more than one passageway.

32. The device for the controlled delivery of the beneficial drug to the biological environment of use according to claim 29, wherein the passageway is a pore formed by leaching a leachable member from the wall.

33. The device for the controlled delivery of the beneficial drug to the biological environment of use according to claim 29, wherein the passageway comprises at least one micropore in a wall comprising a cellulose acylate.

34. The device for the controlled delivery of the beneficial drug to the biological environment of use according to claim 29, wherein the device when in operation in the environment of use, composition (2) comprising the osmotically effective compound and the polymer both imbibe fluid through the wall into the compartment.

35. The device for the controlled delivery of the beneficial drug to the biological environment of use according to claim 29, wherein the shaped wall is formed of a polymeric composition selected from the group consisting of cellulose acetate butyrate and cellulose acetate propionate.

36. The device for the controlled delivery of the beneficial drug to the biological environment of use according to claim 29, wherein the shaped wall is a laminate comprising a semipermeable lamina and a microporous lamina.

37. The device for the controlled delivery of the beneficial drug to the biological environment of use according to claim 29, wherein the environment of use is the gastrointestinal tract and the shaped wall comprises a member selected from the group consisting of cellulose acylate, cellulose diacylate, cellulose triacelate, cellulose acetate, cellulose diacetate, and cellulose triacetate.

38. The device for the controlled delivery of the beneficial drug according to claim 29, wherein the biological environment of use is the vagina or the rectum.

39. The device for the controlled delivery of the beneficial drug according to claim 29, wherein the biological environment is a human and the osmotic device is shaped and sized for oral admittance into the human.

40. The device for the controlled delivery of the beneficial drug according to claim 29, wherein the device when in operation in the environment of use, (1) the composition comprising drug and the polymer imbibes fluid into the compartment and forms a dispensable formulation containing drug and polymer, and (2) the composition comprising osmotically effective compound and polymer imbibe fluid into the compartment and forms in situ a formulation containing compound and polymer, whereby through the combined operations of (1) and (2) the formulation containing drug is delivered through the passage way from the compartment to the exterior of the device over time.

41. The device for the controlled delivery of the beneficial drug according to claim 29, wherein polymer comprising composition (1) is water soluble.

42. The device for the controlled delivery of the beneficial drug according to claim 29, wherein the polymer comprising composition (2) is water soluble.

43. The device for the controlled delivery of the beneficial drug according to claim 29, wherein the beneficial drug is a member selected from the group consisting of mimodipine, nitrendipine, nisoldipine, nicardipine, felodipine, lidoflazine, tiapamil, gallopamil, amlodipine and mioflazine.

44. The device for the controlled delivery of the beneficial drug according to claim 29, wherein the beneficial drug is a nonsteroidal anti-inflammatory drug.

45. The device for the controlled delivery of the beneficial drug according to claim 29, wherein the shaped wall is at least in part microporous.

46. The device for the controlled delivery of the beneficial drug according to claim 29, wherein the shaped wall is microporous.

47. The device for the controlled delivery of the beneficial drug according to claim 29, wherein the beneficial drug is a polypeptide.

48. An device for the controlled delivery of a beneficial drug formulation to a biological environment of use, comprising:
 (a) a shaped wall permeable in at least a part to the passage of an exterior biological fluid and substantially impermeable to the passage of drug formulation, which wall surrounds and forms:
 (b) a compartment comprising: (1) a drug formulation that comprises a drug that is insoluble to very soluble in the biological fluid, an osmotically effective solute that is soluble in the exterior fluid and exhibits an osmotic pressure gradient across the wall against the fluid, and a polymer that imbibes fluid and absorb fluid that enters the compartment, which drug, solute and polymer form a dispensable formulation with fluid that enters the compartment; and, (2) a cooperating formulation that assists in delivering the drug formulation from the device, which cooperating formulation comprises an osmotically effective solute that is soluble in the exterior fluid and exhibits an osmotic pressure gradient across the wall against the fluid and a polymer that imbibes fluid and absorbs fluid that enters the compartment; and,
 (c) a passageway in the semipermable wall connecting the exterior of the device with the interior of the device for delivering the drug formulation from the device to the environment at a controlled rate over prolonged period of time.

49. The osmotic device for the delivery of the beneficial drug formulation according to claim 48, wherein the biological enviromnent of use is a human.

50. The osmotic device for the delivery of the beneficial drug formulation according to claim 48, wherein the biological environment of use is the gastronitestinal tract, and the device is shaped and adapted for oral admittance therein.

51. The osmotic device for the delivery of the beneficial drug formulation according to claim 48, wherein the drug is verapamil.

52. The osmotic device for the delivery of the beneficial drug formulation according to claim 48, wherein the drug is diltiazem.

53. The osmotic device for the delivery of the beneficial drug formulation according to claim 48, wherein the drug is propanolol.

54. The osmotic device for the delivery of the beneficial drug formulation according to claim 48, wherein the drug is ibuprofen.

55. The osmotic device for the delivery of the beneficial drug formulation according to claim 48, wherein the drug is ketoprofen.

56. The osmotic device for the delivery of the beneficial drug formulation according to claim 48, wherein the drug is cephalexin.

57. The osmotic device for the delivery of the beneficial drug formulation according to claim 48, wherein the drug is a member selected from the group consisting of erythromycin, erthromycin lactobionate, erythromycin glucoheptonate and erythromycin estolate.

58. The osmotic device for the delivery of the beneficial drug formulation according to claim 48, wherein the drug is zomepirac.

59. The osmotic device for the delivery of the beneficial drug formulation according to claim 48, wherein the drug is a member selected from the group of cardiovascular drugs consisting of fendriline, perhexiline, gallopamil, prenylamine, captompril, bethamidine and atenolac.

60. The device for the delivery of the beneficial drug formulation according to claim 48, wherein the drug is flurobiprofen.

61. The device for the delivery of the beneficial drug formulation according to claim 48, wherein the drug is present as a therapeutically acceptable salt.

62. A dosage form for delivering at a controlled rate a beneficial drug to biological environment of use, the dosage form comprising:
 (a) a wall comprising in at least a part a composition permeable to the passage of fluid, which wall surrounds and forms:

(b) a compartment comprising a beneficial drug formulation that exhibits an osmotic pressure gradient across the wall against an external biological fluid and forms a dispensable drug formulation with fluid that enters the compartment, and a composition comprising an osmotically effective compound that exhibits an osmotic pressure gradient across the wall against an external fluid for imbibing fluid into the compartment for occupying the compartment; and, (c) a passageway in the wall communicating with the exterior of the dosage form and the compartment for delivering the drug formulation comprising a therapeutically effective amount of drug from the dosage form at a controlled rate over a prolonged period of time.

63. The dosage form for delivering at a controlled rate a beneficial drug to a biological environment of use according to claim 62, wherein the osmotically effective compound is a polymer.

64. The dosage form for delivering at a controlled rate the beneficial drug to a biological environment of use according to claim 62, wherein the osmotically effective compound is a solute.

65. An osmotic device for the delivery at a controlled rate a beneficial drug to a biological environment of use, the osmotic device comprising:
 (a) a wall comprising in at least a part a semipermeable composition permeable to the passage of an exterior fluid present in the environment of use and substantially impermeable to the passage of beneficial drug, the wall surrounding and forming:
 (b) a compartment comprising a beneficial drug formulation that forms a dispensable formulation with biological fluid that enters the osmotic device; and, a composition comprising an osmoticallly effective compound that exhibits an osmotic pressure gradient across the wall against an external fluid and a polymer that exhibits an osmotic pressure gradient across the wall aganist an external fluid; and,
 (c) a passageway in the wall communicating with the exterior of the device and the dispensable formulation comprising the drug for delivering a therapeutically effective amount of drug from the device at a controlled rate over a prolonged period of time.

66. A composition for forming a drug delivery system, comprising: (1) a composition comprising a drug and an osmopolymer that forms with an aqueous fluid a composition dispensable from a drug delivery system; and (2) a composition in laminar arrangement with composition (1), which composition (2) comprises an osmagent and an osmopolymer, and wherein composition (1) and (2) exhibit an osmotic pressure gradient across a semipermeable polymer film against an aqueous fluid.

67. A method for administering a beneficial drug to the gastrointestinal tract of an animal, which method comprises:
 (a) admitting an osmotic device orally into the animal, said osmotic device comprising:
  (1) a wall comprising at least in part a semipermeable composition permeable to the passage of an exterior fluid and substantially impermeable to the passage of drug, which wall surrounds and forms:
  (2) a compartment comprising a first composition comprising a dosage unit amount of a gastrointestinal administrable drug and an osmopolymer that exhibits an osmotic pressure gradient across the wall against an external fluid, and a second composition comprising an osmopolymer that is a different osmopolymer and exhibits an osmotic pressure gradient across the wall against an external fluid;
  (3) at least one osmotic passageway in the wall connecting the exterior of the osmotic device with the first composition; and,
 (b) administering the drug by imbibing fluid through the wall into the first composition to form a dispensable first composition, and by imbibing fluid into the second composition to form a composition that expands against the first composition, whereby through the actions of the compositions the drug is urged through a passageway to the gastrointestinal tract over a prolonged period of time.

68. The method for administering a beneficial drug to the gastrointestinal tract of an animal according to claim 67, wherein the beneficial drug is a member selected from the group consisting of milrinone, amrinone and digoxin.

69. The method for administering a beneficial drug to the gastrointestinal tract of an animal according to claim 67, wherein the beneficial drug is an anterior pituitary suppressant.

70. The method for administering a beneficial drug to the gastrointestinal tract of an animal according to claim 67, wherein the beneficial drug is a steroid.

71. The method for administering a beneficial drug to the gastrointestinal tract of an animal according to claim 67, wherein the beneficial drug is an oral contraceptive.

72. The method for administering a beneficial drug to the gastrointestinal tract of an animal according to claim 67, wherein the beneficial drug is danazol.

73. The method for administering a beneficial drug to the gastrointestinal tract of an animal according to claim 67, wherein the beneficial drug is diltiazem.

74. The method for administering a beneficial drug to the gastronitestinal tract of an animal according to claim 67, wherein the benficial drug is nicardipine.

75. The method for administering a beneficial drug to the gastronitestinal tract of an animal according to claim 67, wherein the wall of the osmotic device comprises in at least a part a layer comprising the beneficial drug on its outer surface.

76. An osmotic device for the administration of the beneficial drug diltiazem to an environment of use, the osmotic device comprising:
 (a) a wall comprising in at least a part a composition pemerable to the passage of fluid, which wall surrounds and defines;
 (b) a compartment;
 (c) a first composition in the compartment, said composition comprising a dosage amount of diltiazem and a pharmaceutically acceptable polymer;
 (d) a second composition in the compartment, said composition comprising an osmopolymer that expands in the presence of fluid; and,
 (e) at least one passageway in the wall communicating with the compartment and the exterior of the device for delivering the first composition comprising the beneficial drug diltiazem to the envrionment of use over time.

77. The osmotic device for the administration of the beneficial drug diltiazem to the environment of use according to claim 76, wherein the wall of the osmotic device comprises in at least a part a layer comprising the beneficial drug diltiazem on its outer surface.

78. An osmotic device for the administration of the benficial drug nicardipine to an environment of use, the osmotic device comprising:
  (a) a wall comprising in at least a part a nontoxic composition permeable to the passage of fluid, which wall surrounds and defines;
  (b) a compartment;
  (c) a first composition in the compartment, said first composition comprising a dosage amount of the beneficial drug nicardipine and a pharmaceutically acceptable polymer;
  (d) a second composition in the compartment, which composition comprises an osmopolymer that expands in the presence of fluid that enters the compartment; and,
  (e) at least one passageway in the wall communicating with the composition comprising the beneficial drug nicardipine to the environment of use over time.

79. The osmotic device for the administration of the beneficial drug nicardipine to the environment of use according to claim 78, wherein the wall of the osmotic device comprises in at least a part a layer comprising the beneficial drug nicardipine on its outer surface.

* * * * *